United States Patent
Singh

(10) Patent No.: US 11,207,103 B2
(45) Date of Patent: Dec. 28, 2021

(54) METHODS AND SYSTEMS FOR ADJUSTING AN EXTERNAL FIXATION FRAME

(71) Applicant: Stryker European Operations Holdings LLC, Wilmington, DE (US)

(72) Inventor: Manoj Kumar Singh, Mahwah, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 245 days.

(21) Appl. No.: 16/667,974

(22) Filed: Oct. 30, 2019

(65) Prior Publication Data

US 2020/0060728 A1   Feb. 27, 2020

Related U.S. Application Data

(60) Division of application No. 15/895,117, filed on Feb. 13, 2018, now Pat. No. 10,492,832, which is a
(Continued)

(51) Int. Cl.
  *A61B 17/62* (2006.01)
  *A61B 34/00* (2016.01)
  (Continued)

(52) U.S. Cl.
  CPC .............. *A61B 17/62* (2013.01); *A61B 17/88* (2013.01); *A61B 17/8875* (2013.01);
  (Continued)

(58) Field of Classification Search
  CPC ..... A61B 17/62; A61B 17/88; A61B 17/8875; A61B 2017/00398; A61B 2017/00725;
  (Continued)

(56) References Cited

U.S. PATENT DOCUMENTS

| 2,692,523 A | 10/1954 | Finn |
| 4,365,624 A | 12/1982 | Jaquet |

(Continued)

FOREIGN PATENT DOCUMENTS

EP   2252222 A1   11/2010

OTHER PUBLICATIONS

European Search Report for Application No. 15190728.4 dated Mar. 30, 2016.

(Continued)

*Primary Examiner* — Pedro Philogene
(74) *Attorney, Agent, or Firm* — Lerner, David, Littenberg, Krumholz & Mentlik, LLP

(57) ABSTRACT

A tool for implementing a correction plan in an external fixation frame having a plurality of adjustment elements or screws, for example, generally includes a driver, a motor, a controller, and a processor. The driver is adapted to engage and rotate each of the screws. The motor is coupled the driver and adapted to rotate the driver. The controller is connected to the motor and configured to control operation of the motor. The controller may determine whether the tool is engaged with a strut and which strut is engaged, and may determine how much the strut has rotated, taking into account intentional or unintentional manual rotation of the tool. The tool may also include features to help ensure proper engagement between the drive and the strut. Variations may be provided in which similar functionality is provided with manual rotation of a motorless tool.

10 Claims, 14 Drawing Sheets

Related U.S. Application Data continuation of application No. 14/523,150, filed on Oct. 24, 2014, now Pat. No. 9,987,043.

(51) Int. Cl.
*A61B 90/00* (2016.01)
*A61B 17/88* (2006.01)
*A61B 17/00* (2006.01)
*A61B 17/56* (2006.01)

(52) U.S. Cl.
CPC .............. *A61B 34/25* (2016.02); *A61B 90/06* (2016.02); *A61B 90/37* (2016.02); *A61B 90/39* (2016.02); *A61B 2017/00398* (2013.01); *A61B 2017/00725* (2013.01); *A61B 2017/00734* (2013.01); *A61B 2017/564* (2013.01); *A61B 2034/252* (2016.02); *A61B 2090/031* (2016.02); *A61B 2090/061* (2016.02); *A61B 2090/063* (2016.02); *A61B 2090/064* (2016.02); *A61B 2090/067* (2016.02); *A61B 2090/0807* (2016.02); *A61B 2090/0812* (2016.02)

(58) Field of Classification Search
CPC .... A61B 2017/00734; A61B 2017/564; A61B 34/25; A61B 2034/252; A61B 90/37; A61B 90/39; A61B 2090/031; A61B 2090/061; A61B 2090/063; A61B 2090/064; A61B 2090/067; A61B 2090/0807; A61B 2090/0812
See application file for complete search history.

(56) References Cited

U.S. PATENT DOCUMENTS

| | | |
|---|---|---|
| 4,570,625 A | 2/1986 | Harris et al. |
| 4,615,338 A | 10/1986 | Ilizarov et al. |
| 4,973,331 A | 11/1990 | Pursley et al. |
| 4,978,348 A | 12/1990 | Ilizarov |
| 5,014,794 A | 5/1991 | Hansson |
| 5,108,393 A | 4/1992 | Ruffa |
| 5,108,394 A | 4/1992 | Kurokawa et al. |
| 5,156,605 A | 10/1992 | Pursley et al. |
| 5,180,380 A | 1/1993 | Pursley et al. |
| 5,334,202 A | 8/1994 | Carter |
| 5,437,668 A | 8/1995 | Aronson et al. |
| 5,702,389 A | 12/1997 | Taylor et al. |
| 5,788,695 A | 8/1998 | Richardson |
| 5,971,984 A | 10/1999 | Taylor et al. |
| 6,017,354 A | 1/2000 | Culp et al. |
| 6,033,412 A | 3/2000 | Losken et al. |
| 6,132,435 A | 10/2000 | Young |
| 7,243,581 B1 | 7/2007 | Gao |
| 7,272,998 B1 | 9/2007 | Gauthier |
| 7,559,951 B2 | 7/2009 | DiSilvestro et al. |
| 7,955,334 B2 | 6/2011 | Steiner et al. |
| 8,157,800 B2 | 4/2012 | Vvedensky et al. |
| 8,167,880 B2 | 5/2012 | Vasta |
| 8,282,652 B2 | 10/2012 | Mackenzi et al. |
| 8,333,766 B2 | 12/2012 | Edelhauser et al. |
| 8,702,705 B2 | 4/2014 | Ziran et al. |
| 8,714,056 B2 | 5/2014 | Landowski |
| 8,864,750 B2 * | 10/2014 | Ross .................... A61B 90/96 606/1 |
| 9,511,484 B2 | 12/2016 | Marchant et al. |
| 9,987,043 B2 | 6/2018 | Singh |
| 9,987,066 B2 | 6/2018 | Stad et al. |
| 10,194,944 B2 | 2/2019 | Edelhauser et al. |
| 2002/0010465 A1 | 1/2002 | Koo et al. |
| 2003/0149378 A1 | 8/2003 | Peabody et al. |
| 2003/0191466 A1 | 10/2003 | Austin et al. |
| 2003/0199856 A1 | 10/2003 | Hill et al. |
| 2005/0215997 A1 | 9/2005 | Austin et al. |
| 2006/0207118 A1 | 9/2006 | Kim |
| 2007/0085496 A1 | 4/2007 | Philipp et al. |
| 2007/0225704 A1 | 9/2007 | Ziran et al. |
| 2007/0233134 A1 | 10/2007 | Bastian et al. |
| 2008/0178713 A1 | 7/2008 | Long et al. |
| 2008/0243134 A1 | 10/2008 | Limberg et al. |
| 2008/0281332 A1 | 11/2008 | Taylor |
| 2010/0121323 A1 | 5/2010 | Pool et al. |
| 2010/0264864 A1 | 10/2010 | Hafner et al. |
| 2011/0004199 A1 | 1/2011 | Ross et al. |
| 2012/0041439 A1 | 2/2012 | Singh et al. |
| 2012/0059425 A1 | 3/2012 | Biedermann |
| 2012/0109143 A1 | 5/2012 | Steele et al. |
| 2012/0330312 A1 | 12/2012 | Burgherr et al. |
| 2013/0253513 A1 | 9/2013 | Ross et al. |
| 2013/0289575 A1 | 10/2013 | Edelhauser et al. |
| 2014/0018816 A1 | 1/2014 | Fenn et al. |
| 2014/0236153 A1 | 8/2014 | Edelhauser |
| 2014/0276891 A1 | 9/2014 | Defalco et al. |
| 2014/0277203 A1 | 9/2014 | Atoulikian et al. |
| 2015/0045840 A1 | 2/2015 | Vaucher et al. |

OTHER PUBLICATIONS

Extended European Search Report for Application No. 16179304.7 dated Dec. 8, 2016.

* cited by examiner

| Date | Day | Strut 1 (Red) | Strut 2 (Orange) | Strut 3 (Yellow) | Strut 4 (Green) | Strut 5 (Blue) | Strut 6 (Violet) | View |
|---|---|---|---|---|---|---|---|---|
| 01/01/01 | 0 | 150 | 145 | 140 | 135 | 160 | 160 | View |
| 01/02/01 | 1 | 151 | 144 | 146 | 138 | 159 | 156 | View |
| 01/03/01 | 2 | 151 | 142 | 151 | 141 | 158 | 152 | View |
| 01/04/01 | 3 | 152 | 141 | 157 | 144 | 158 | 148 | View |
| 01/05/01 | 4 | 153 | 139 | 162 | 147 | 157 | 144 | View |
| 01/06/01 | 5 | 153 | 138 | 168 | 150 | 156 | 140 | View |
| 01/07/01 | 6 | 154 | 137 | 173 | 154 | 155 | 137 | View |
| 01/08/01 | 7 | 155 | 135 | 179 | 157 | 154 | 133 | View |
| 01/09/01 | 8 | 156 | 134 | 184 | 160 | 154 | 129 | View |
| 01/10/01 | 9 | 156 | 132 | 190 | 163 | 153 | 125 | View |
| 01/11/01 | 10 | 157 | 131 | 195 | 166 | 152 | 121 | View |

FIG. 3

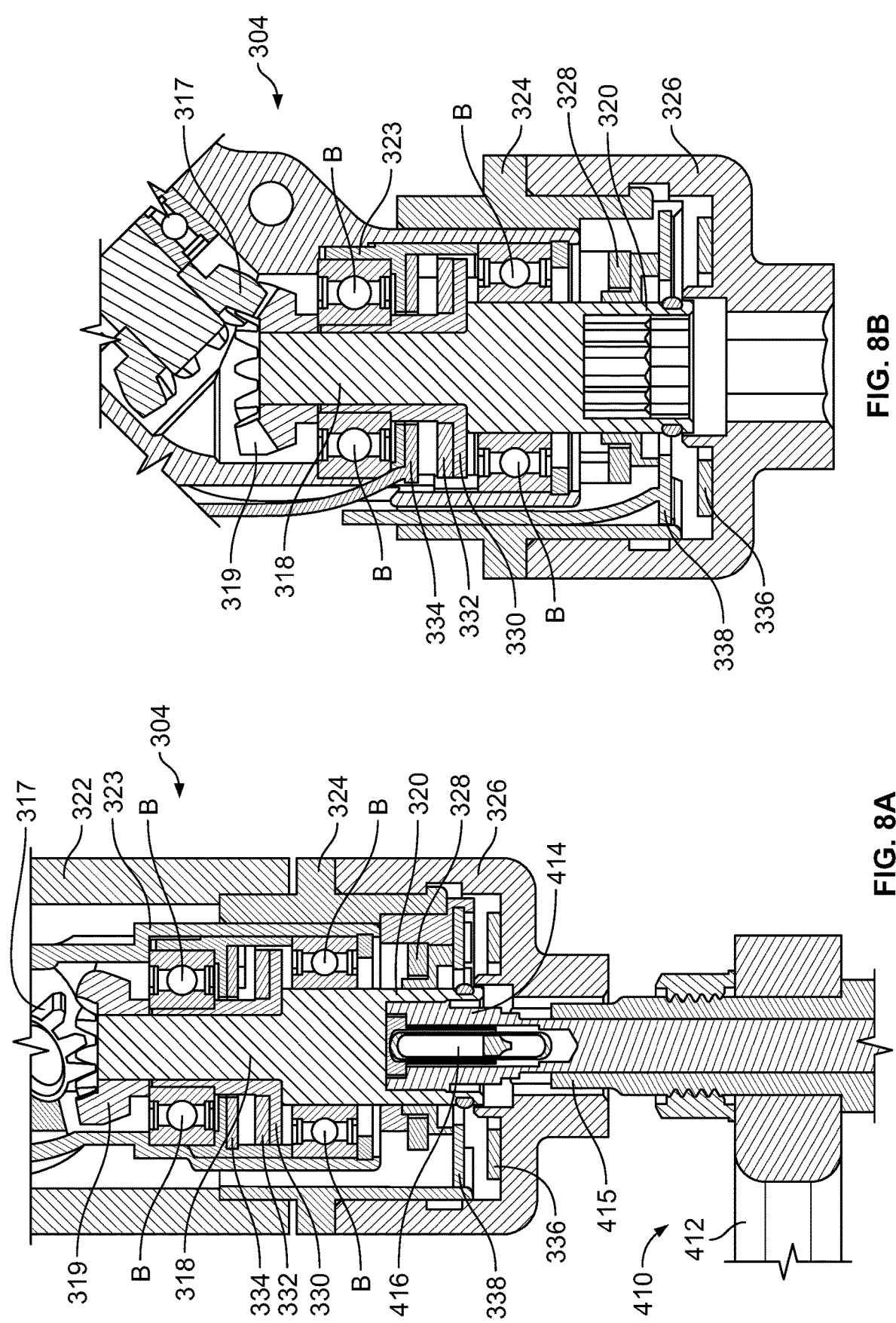

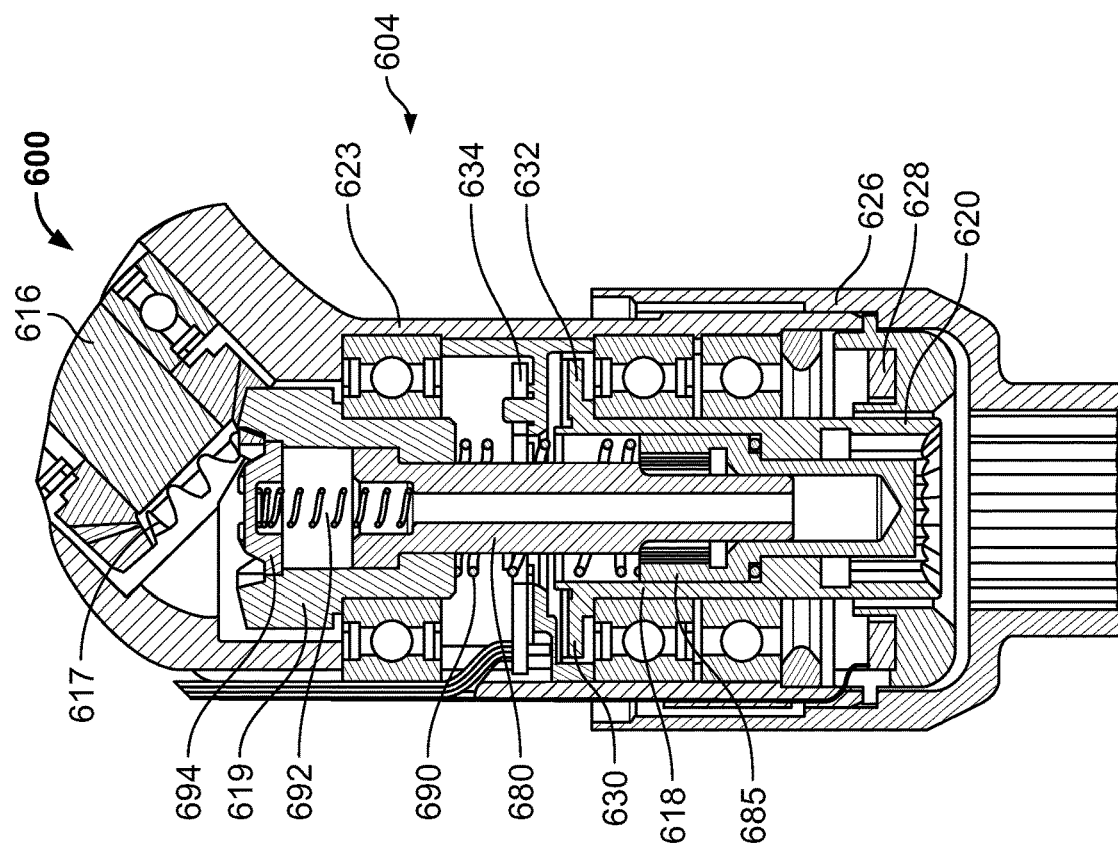

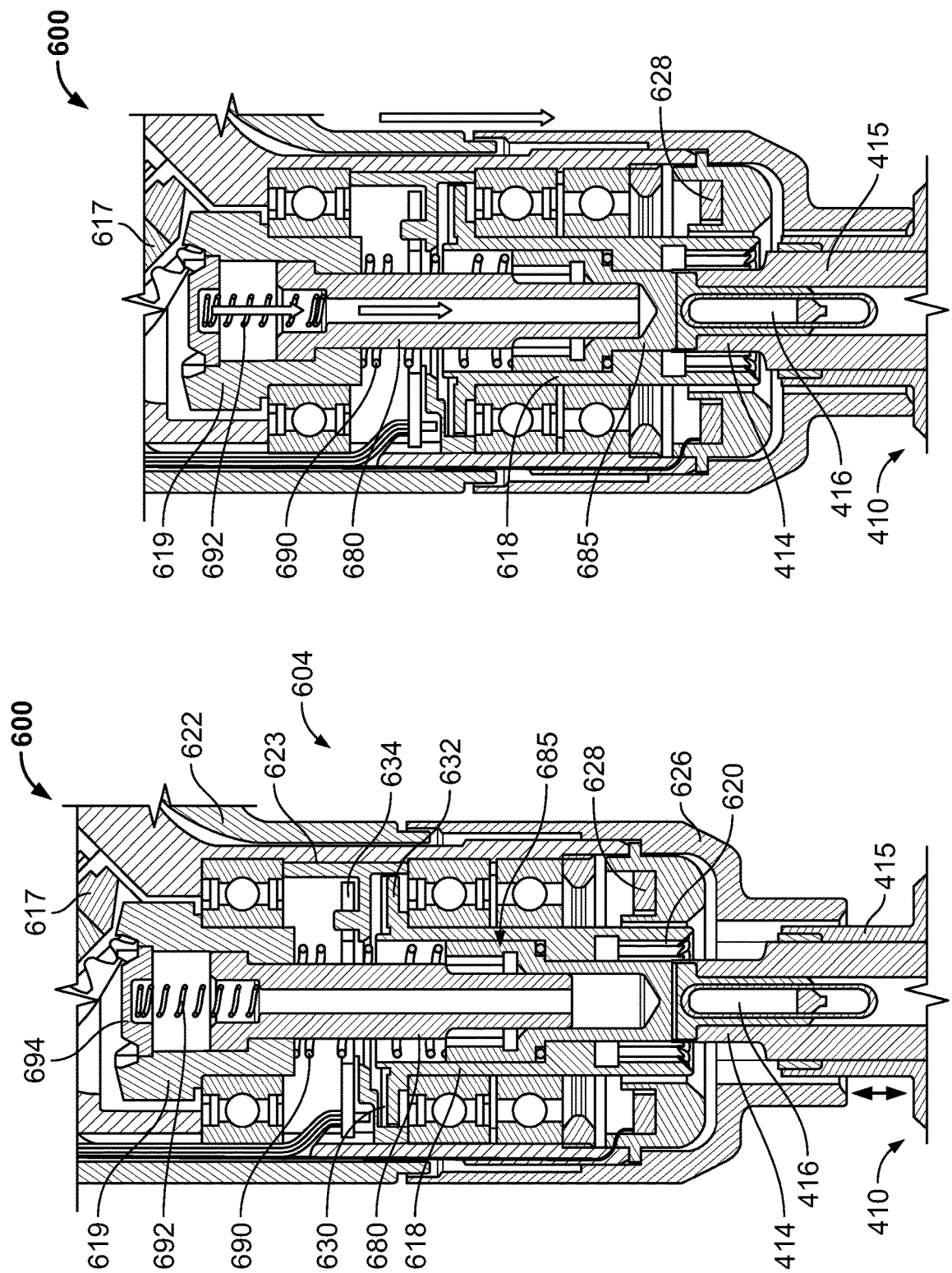

METHODS AND SYSTEMS FOR ADJUSTING AN EXTERNAL FIXATION FRAME

CROSS-REFERENCE TO RELATED APPLICATIONS

This application is a divisional of U.S. patent application Ser. No. 15/895,117, filed Feb. 13, 2018, which is continuation of U.S. patent application Ser. No. 14/523,150, filed on Oct. 24, 2014 and issued as U.S. Pat. No. 9,987,043 on Jun. 5, 2018, the disclosures of which are hereby incorporated by reference herein.

BACKGROUND OF THE DISCLOSURE

The present disclosure relates to methods, tools, and systems for adjusting an external fixation frame. More particularly, the present disclosure relates to methods, tools, and systems for repositioning the components of an external fixation frame according to a correction plan.

The external fixation market can be divided into two major segments: acute trauma and reconstructive. The trauma segment generally includes modular fixators having fewer components and structured for rapid application to a patient. These frames may be used for temporizing fixation and may only be on the patient for hours or days.

The reconstructive segment includes ring fixators, such as the Ilizarov frame, for example. Such frames are shown in U.S. Pat. Nos. 4,365,624, 4,615,338, 4,978,348, 5,702,389, and 5,971,984. Ring fixators may be used with a combination of pins and wires to achieve a variety of polyaxial pin/wire attachments that provide stability. They can achieve a full six degrees of freedom and can correct primary deformities without creating secondary deformities. Rotational deformities may also be treated with ring fixators. However, mastery of the techniques involved with using ring fixators, as well as the products themselves, can be a long and daunting process.

At times, it may be necessary to realign, reposition, and/or securely hold two bone elements relative to one another. For example, in the practice of medicine, bone fragments and the like are sometimes aligned, realigned, and/or repositioned to restore boney continuity and skeletal function. At times, this may be accomplished by sudden maneuver, followed by skeletal stabilization with cast, plate and screws, intramedullary devices, or external skeletal fixators.

A bone fragment can be moved, in general, from its original position as in a nonunion or malunion or from its intended position as in congenital deformities along six separate movements or degrees of freedom, a combination of three orthogonal translational axes (e.g., typical "X," "Y" and "Z" axes) and three orthogonal rotational axes (e.g., rotation about such typical "X," "Y" and "Z" axes).

External fixation devices may be attached to the boney skeleton with threaded and/or smooth pins and/or threaded and/or smooth and/or beaded wires. Such constructs may be referred to as orthopaedic external fixators or external skeletal fixators. External fixators may be utilized to treat acute fractures of the skeleton, soft tissue injuries, delayed union of the skeleton when bones are slow to heal, nonunion of the skeleton when bones have not healed, malunion whereby broken or fractures bones have healed in a malposition, congenital deformities whereby bones develop a malposition, and bone lengthening, widening, or twisting.

A circumferential external fixator system was disclosed by G. A. Ilizarov during the early 1950s. The Ilizarov system includes at least two rings or "halos" that encircle a patient's body member (e.g., a patient's leg), connecting rods extending between the two rings, transfixation pins that extend through the patient's boney structure, and connectors for connecting the transfixation pins to the rings. Use of the Ilizarov system to deal with angulation, translation, and rotation is disclosed in "Basic Ilizarov Techniques," *Techniques in Orthopaedics®*, Vol. 5, No. 4, December 1990, pp. 55-59.

Often, orthopaedic external fixators such as Ilizarov fixators must be repositioned after their initial application. Such modification may be necessary to convert from one correctional axis to another or to convert from an initial adjustment type of fixator to a weight bearing type of fixator, some of the correctional configurations not being stable enough for weight bearing.

A "Steward platform" is a fully parallel mechanism used in flight and automotive simulators, robotic end-effectors, and other applications requiring spatial mechanisms with high structural stiffness and includes a base platform, a top platform, and six variable limbs extending between the base and top platforms. See S. V. Sreenivasan et al., "Closed-Form Direct Displacement Analysis of a 6-6 Stewart Platform," *Mech. Mach. Theory*, Vol. 29, No. 6, pp. 855-864, 1994.

Taylor et al. U.S. Pat. No. 5,702,389, which entire disclosure is hereby incorporated by reference herein, relates to a fixator that can be adjusted incrementally in six axes by changing strut lengths only, without requiring joints to be unclamped, etc. This patent includes a first ring member or swash plate for attachment relative to a first bone element; a second ring member or swash plate for attachment relative to a second bone element. Six adjustable length struts having first ends movably attached to the first member and second ends movably attached to the second member are provided. The first ends of the first and second struts are joined relative to one another so that movement of the first end of one of the first and second struts will cause a corresponding movement of the first end of the other strut, with the first ends of the third and fourth struts joined relative to one another so that movement of the first end of one of the third and fourth struts will cause a corresponding movement of the first end of the other strut. The third and fourth struts and fifth and sixth struts are similarly joined. Second ends of the first and sixth struts joined relative to one another so that movement of the second end of one of the first and sixth struts will cause a corresponding movement of the second end of the other strut. Second ends of the second and third struts and fourth and fifth struts are formed in a similar manner. Thus, changing the length of the struts effects the positions of the bone segments.

As discussed above, most external fixators should be adjusted over a period of time to reposition bone segments. The adjustment of the external fixation may be implemented according to a "prescription" or correction plan. Physicians may adjust the external fixator at precise times over a period of time (e.g., on a daily basis for three weeks). Patients, however, may not desire to visit the physician's office every time an adjustment is needed. For this reason, external fixators may be adjusted by the patients themselves without the assistance of a physician. The adjustment of the external fixator should nonetheless strictly comply with the predetermined correction plan. However, patients may not adjust their own external fixator according to the correction plan for a variety of reasons. For instance, patients may not understand how to use the external fixator correctly. In addition, when the patients themselves adjust the external fixators, physicians may not even know whether patients are in fact adjusting the external fixators according to the correction plan. For the foregoing reasons, it is desirable to provide a tool, system, and/or method for helping a patient implement a correction plan in an external fixator.

BRIEF SUMMARY OF THE INVENTION

According to one aspect of the disclosure, a tool for actuating one or more of a plurality of adjustment elements of an external fixation frame includes an identification mechanism adapted to identify each of the plurality of adjustment elements. A driving element may be adapted to actuate one or more of the plurality of adjustment elements according to instructions received or processed by the tool. A motor may be operably coupled to the driving element. A first encoder may be adapted to track actuation of each of the adjustment elements caused by the motor. A second rotary encoder may be adapted to track rotation of the plurality of adjustment elements caused by manual rotation of the tool. The tool may additionally include a processor configured to receive correction plan data including a schedule of adjustment times and degree of rotation of each of the plurality of adjustment elements, receive identification data from the identification mechanism, and determine a degree of rotation of at least one of the plurality of adjustment elements based on information supplied by the first rotary encoder and the second rotary encoder. In addition or alternatively, the processor may be further configured to instruct the motor to deactivate after determining the degree of rotation of the one of the plurality of adjustment elements has reached a predetermined limit. In addition or alternatively, the housing may include a first housing portion and a second housing portion rotatably coupled to the first housing portion. In addition or alternatively, the first rotary encoder may be at least partially positioned on the first housing portion and the second rotary encoder may be at least partially positioned the second housing portion. In addition or alternatively, the driving element may include a first output shaft coupled to the motor and a second output shaft operably coupled to the first output shaft. In addition or alternatively, the second output shaft may include a connector portion configured to couple to a head of at least one of the plurality of adjustment elements and a distal portion of the housing may include a connector portion configured to couple to a body of at least one of the plurality of adjustment elements.

According to another aspect of the disclosure, a method of implementing a correction plan in an external fixation frame having a plurality of adjustment elements may include engaging a driving element of a tool to one of the plurality of adjustment elements in a first engagement position, wherein, in the first engagement position, an identification mechanism of the tool does not recognize an identification tag of the adjustment element. A force may be applied to the tool to transition the tool from the first engagement position to the second engagement position, wherein, in the second engagement position, the identification mechanism of the tool does recognize the identification tag of the adjustment element. A motor of the tool may be actuated to drive the driving element and rotate the adjustment element when the tool is in the second engagement position. In addition, the step of engaging the driving element of the tool to the one adjustment element in the first engagement position may include positioning a distal end of a sliding member to the one adjustment element, the sliding member being at least partially positioned within the driving element. In addition or alternatively, the step of transitioning the tool from the first engagement position to the second engagement position may include moving a housing of the tool distally with respect to the sliding member while the distal end of the sliding member remains in contact with the one adjustment element. In addition or alternatively, the step of engaging the drive element of the tool to the one adjustment element in the first engagement position may include positioning a distal end of a guide member to the one adjustment element, the guide member being at least partially positioned within the driving element. In addition or alternatively, the step of transitioning the tool from the first engagement position to the second engagement position may include moving a housing of the tool distally with respect to the guide member while the distal end of the guide member remains in contact with the one adjustment element. In addition or alternatively, as the housing of the tool is moved distally with respect to the guide member, a slide member at least partially positioned within the driving element may slide distally into the guide member. In addition or alternatively, the step of actuating the motor of the tool to drive the driving element and rotate the adjustment element may be continued until a processor of the tool determines the adjustment element has rotated a predetermined amount and instructs the motor to deactivate.

According to a further aspect of the disclosure, a tool for tracking progress of a correction plan in an external fixation frame having a plurality of adjustment elements may include a bushing for fixedly coupling to a rotatable head of one of the adjustment elements, a first component of a rotary encoder fixedly coupled to the bushing; and a second component of a rotary encoder positioned adjacent the first component and fixedly coupled to a body of the one adjustment element, the first and second components being rotatable relative to one another. In addition, the bushing may include a recess for accepting the head of the one adjustment element. In addition or alternatively, the tool may include a battery within the tool to power components of the tool. In addition or alternatively, the tool may include a display capable of indicating a degree of rotation of the head of the one adjustment element.

BRIEF DESCRIPTION OF THE DRAWINGS

Various embodiments of the present disclosure will now be described with reference to the appended drawings. It is appreciated that these drawings depict only some embodiments of the invention and are therefore not to be considered limiting of its scope.

FIG. 3 is an exemplary correction plan in a table form;

FIG. 8A is a sectional view of the distal end of the tool of FIG. 7A engaged with the strut of FIG. 6B;

FIG. 8B is an isolated sectional view of the distal end of the tool of FIG. 7A;

FIG. 9C is a sectional view of a manual version of the tool of FIG. 9A in an initial engagement position;

FIG. 10A is an isolated sectional view of a distal end of a tool according to a further aspect of the disclosure;

FIG. 10B is sectional view of the distal end of the tool of FIG. 10A engaged to the strut of FIG. 6B in an initial engagement position;

FIG. 10C is a sectional view of the distal end of the tool of FIG. 10A engaged with the strut of FIG. 6B in a final engagement position;

DETAILED DESCRIPTION

Figure 1:
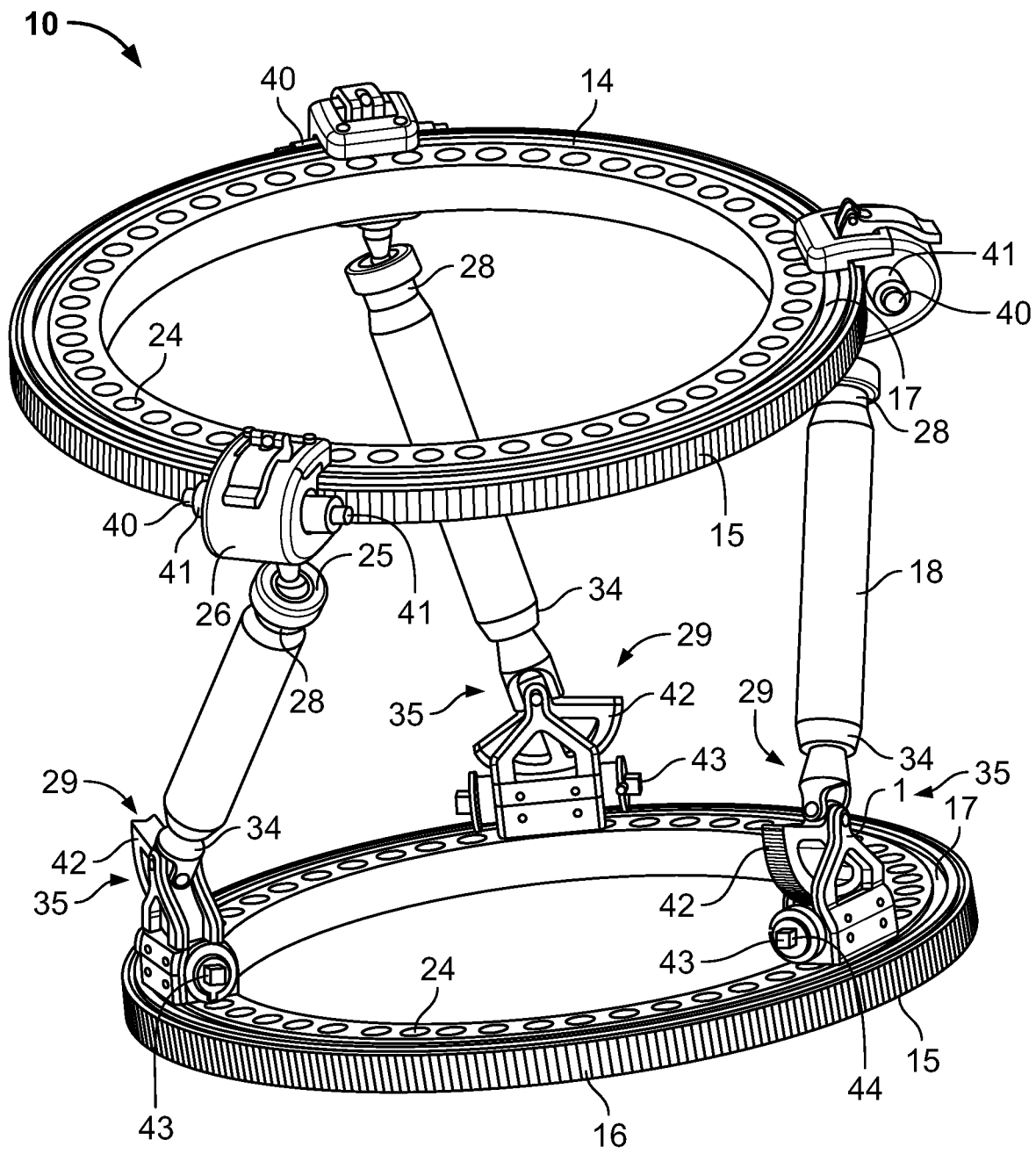
FIG. 1 is an isometric view of an external fixation frame.

The present disclosure describes in detail embodiments of methods and systems for adjusting an external fixation frame with reference to the drawings in which like reference numerals designate identical or substantially similar parts in each view. As used herein, "clinician" refers to a physician, surgeon, nurse or other care provider and may include support personnel. Also, as used herein, when the term "distal" is used with reference to a device, the term refers to a location relatively far away from a user of the device, while the term "proximal" refers to a location relative close to the user.

FIG. 1 illustrates one example of an external fixation frame 10 that may be utilized with any long bone, in particular, the tibia and the femur, which includes a first ring 14 and a second ring 16. Although rings 14 and 16 are illustrated with a closed circular shape, other types of rings, such as open or non-circular rings may be suitable for use with other external fixation frames. In operation, first ring 14 moves relative to second ring 16 during a deformity correction process. In some embodiments, both rings 14, 16 are identical. Rings 14 and 16 may each include a worm gear 15 formed around an outer circumference. Two grooves 17 may be formed in the upper and lower surfaces of ring 14 around its circumference adjacent the worm gear 15. Ring 14 (or 16) may include a multi-level configuration with the upper and lower surfaces having alternate steps including through holes 24. In certain embodiments, rings 14 and 16 are connected by three variable length struts 18. The three struts 18 have first ends 28 mounted to the first ring 14 via a connector 25 coupled to a sliding or shuttle unit 26, which is circumferentially moveable around ring 14. In several embodiments, the first ends 28 are connected to sliding or shuttle units 26 by a connector 25 having a ball or spherical joint. The rings 14 and 16 may be connected to a bone (e.g., tibia) by a plurality of bone pins or wires (not shown). In some embodiments, the pins or wires are connected to each ring 14, 16 by connection elements, which are located in one or more of a plurality of through holes 24 around the circumference of the rings 14 and 16. Although holes 24 are shown, any structure which locates the pins or wires with respect to the circumference of rings 14 and 16 can be utilized. Lower ends 34 of struts 18 may be connected to lower ring 16 by standard universal-joints 35, which allow free rotation about only two axes rather than the three axes of the spherical joint at the first strut end 28.

Ring 14 may be coupled to a first bone element via pins or wires and, similarly, ring 16 may be coupled to a second bone element by similar pins or wires. Shuttle units 26 are slidable about ring 14 in a track. Each shuttle unit 26 may include a worm or screw 40 configured to mesh with worm gear 15 of first ring 14. Each screw 40 can be driven by a driver, such as a manual driver or automated driver described herein in connection with FIGS. 7A-10D.

Identification tags 41, such as RFID tags, may be disposed on both sides of each screw 40. Each identification tag 41 may store identification data and may be adapted to generate a signal indicative of the identification data of a particular screw 40. For instance, the identification data may include a number or letter assigned to a specific screw 40, and may be a completely unique identifier. As is discussed in greater detail below in connection with FIGS. 7A-10B, a signal reader of a tool may be adapted to read the signals generated from each identification tag 41 to identify the screw 40 associated with a particular identification tag 41. In operation, rotation of screw 40 causes shuttle unit 26 to slide about ring 14, thus changing the position of strut 18. A second connector 29 between strut 18 and ring 16 may have a standard universal joint 35, which allows the strut to rotate freely about two axes, which may be oriented perpendicular to each other. Each universal joint 35 may include a gear portion 42 and screw 43. Screw 43 is adapted to engage gear portion 42 and, similar to screw 40, may be rotated by a driver.

Identification tags 44, such as RFID tags, may be disposed on both sides of each screw 43. Each identification tag 44 may be adapted to produce and/or send a signal containing identification data. The identification data may include information distinguishing a particular screw 43 from others screws of external fixation frame 10. Thus, each identification tag 44 may be configured to generate a signal indicative of the location and identity of a particular screw 43 with respect to the entire external fixation frame 10. In addition, the signal generated by identification tag 44 may be indicative of the side of the screw 43 where the tag is located. Similar to identification tags 41, identification tags 44 may be read by a signal reader in order to identify the screw 43. Although the drawings show screws 40 and 43, external fixation frame may alternatively include any drive element capable of being driven by a driver. The signal reader and identification tags 41 and 44 collectively form an identification mechanism adapted to identify each and every screw 40 and 43 of external fixation frame 10. During operation, rotation of screw 43 causes gear portion 42 to pivot about a pin 1, thereby causing strut 18 to change its orientation relative to the rings 14 and 16. Thus, each of the three sliding shuttle units 26 may be independently controlled and the three connectors 29 at the second ring 16 may be independently controlled so that the ring 14, and therefore the bone element attached to ring 14, can be positioned in proper alignment with ring 16 and the bone element attached to ring 16. Rings 14 and 16 can be repositioned after their initial alignment as desired by the surgeon. Each strut 18 may have a variable or fixed length.

Figure 2:
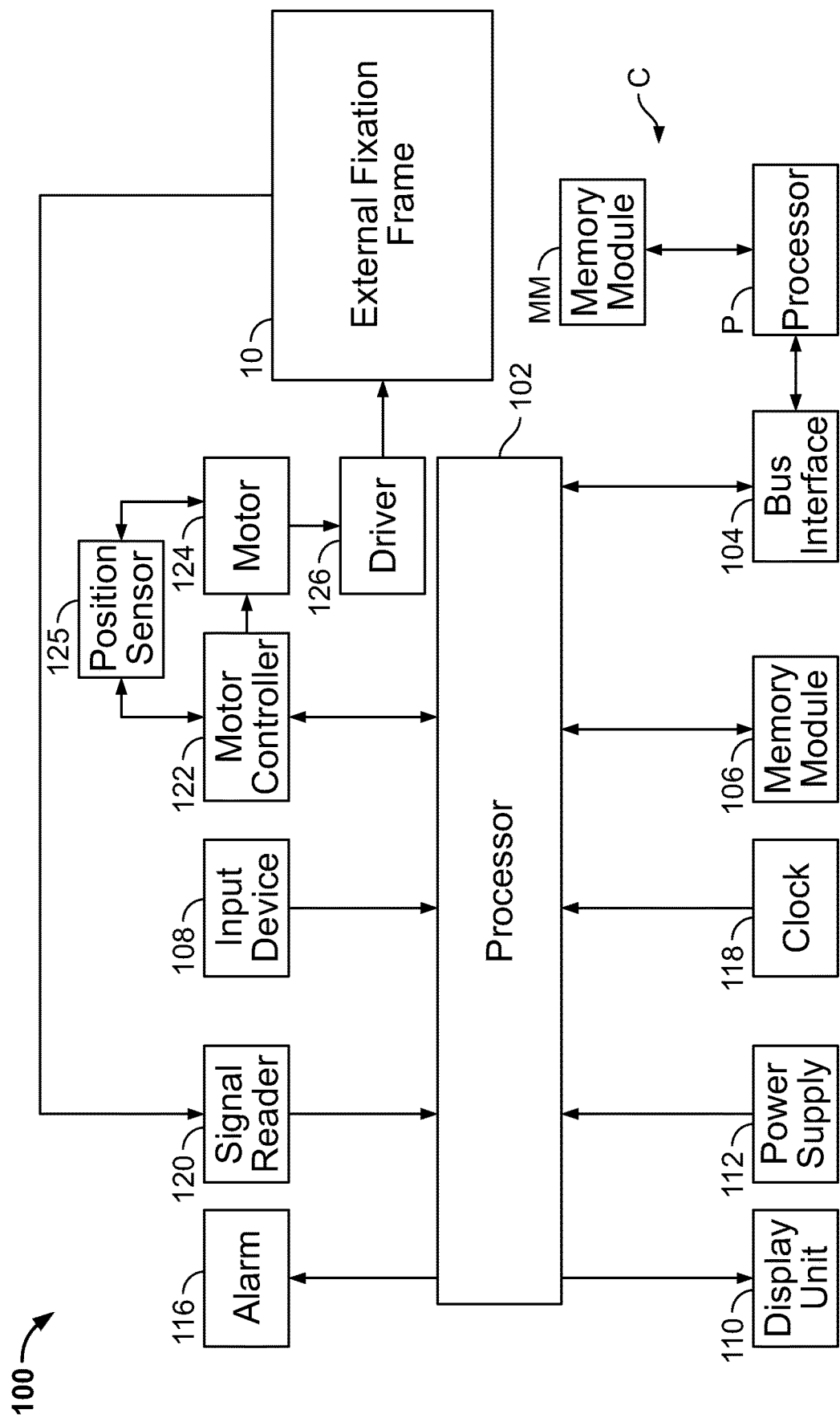
FIG. 2 a schematic diagram of a system for adjusting an external fixation frame in accordance with an embodiment of the present disclosure.

FIG. 2 schematically depicts a tool or system 100 for adjusting external fixation frame 10. It should be understood that, although one particular embodiment of external fixation frame 10 is described in connection with FIG. 1, tool 100 may be used with other types of external fixation frames having screw-type mechanisms that, upon rotation, cause a relative change in position between ring members of an external fixation frame. One suitable external fixation frame is described in detail in U.S. Pat. No. 8,333,766, the entire disclosure of which is hereby incorporated by reference herein. Another suitable external fixation frame is described in U.S. Pat. No. 7,955,334, the entire disclosure of which is hereby incorporated herein by reference. The mathematics of the incremental adjustments is described in these applications.

In general, the tool 100 may include a processor 102, such as a microprocessor or central processing unit, capable of executing instructions for adjusting an external fixation frame 10. The processor 102 may include any suitable bus interface 104 for establishing communication between tool 100 and an external host computer C, such as a personal computer. Suitable bus interfaces 104, include, but are not limited to Universal Serial Bus (USB), a serial port, a parallel port, IEEE 1394 interface and Ethernet bus. Regardless of its specific type, bus interface 104 allows transfer of data between tool 100 and host computer C. Host computer C may include a processor P for executing instructions and a memory module MM for storing data. The bus interface 104 allows data stored on memory module MM to be transferred to the tool 100. The data transfer between tool 100 and host computer C may be performed directly or indirectly. For example, data may be transferred between tool 100 and host computer C through a network, such as the Internet. The tool 100 may include a memory module 106 to store data, including data transferred from host computer C. The processor 102 can therefore retrieve and process data from memory module 106. If host computer C is connected to tool 100 through bus interface 104, the processor 102 can also retrieve and process data stored on the memory module MM of host computer 300.

With continued reference to FIG. 2, tool 100 may further include an input device 108 for inputting information. Input device 108 is adapted to accept instructions from a user and is connected to processor 102. In some embodiments, input device 108 may include a keypad having a plurality of alphanumeric keys and/or function keys configured to be actuated by users. Input device 108 may additionally or alternatively include any other suitable device, means or mechanisms for entering information into tool 100, such a computer mouse, touchpad, trackball, touch screen, etc. In one embodiment, input device 108 includes a touchpad having a flat, touch sensitive screen, which tracks the movement of a finger or stylus across it.

The tool 100 may include a display unit 110 capable of displaying images. The display unit 110 is connected to processor 102 and may include liquid crystal display (LCD) panel. As discussed in detail below, display unit 100 may show information pertinent to the use of tool 100.

Any suitable power supply 112 may be coupled to processor 102 for energizing tool 100. Power supply 112 may include a DC or AC power source and/or a battery. The battery may be rechargeable.

The tool 100 may additionally include an alarm 116 capable of generating a visual signal, an audio signal, and/or a tactile signal. The alarm 116 is connected to processor 102. As discussed in detail below, processor 102 can execute instructions to activate alarm 116. Alarm 116 may include a buzzer or any other device, means, or mechanism adapted for generating a sound or a vibration. As used herein, the term "sound" refers to one or more audio signals across the audible frequency range. Processor 102 may be connected to a clock 118 for measuring time. Clock 118 allows the processor 102 to, for example, actuate the alarm 116 at specified times.

The tool 100 may further include a signal reader 120, such as radio-frequency identification (RFID) reader, capable of reading a signal from a radio-frequency transmitter on each drive element on the frame of, as described below. This signal is indicative of the identification of a specific component, such as a screw, worm gear, or strut of the external fixation frame 10. For example, the screws may be identified by one or more numbers and/or letters. As discussed in detail below, each worm gear may have one or more identification tags, such as an RFID tag, configured to send a signal to be read by the signal reader 120.

The screws of external fixation frame 10 may be rotated by a driver 126 of tool 100. Driver 126 is adapted to engage and rotate the screws of external fixation frame 10. In certain embodiments, a motor 124 is connected to the driver 126. Upon activation, motor 124 can rotate driver 126. The operation and activation of motor 124 is controlled by a motor controller 122 connected to processor 102. The motor controller 122 may be electronically connected to an angular position sensor 125. Angular position sensor 125 may include a synchro, a resolver, a rotary variable differential transformer (RVDT), a rotary potentiometer and/or any suitable rotary encoder. Suitable rotary encoders for angular position sensor 125 include, but are not limited to, a quadrature encoder and an absolute encoder. The angular position sensor 125 may be disposed on the shaft of motor 124, on the driver 126, or on the screws. Regardless of its location, the angular position sensor 125 can determine the angular position of the driver 126 and the screw attached to the driver. During operation, motor controller 122 controls the operation of driver 126 based on the instructions received from processor 102 and signals received from angular position sensor 125. The driver 126 in turns rotates a screw to adjust external fixation frame 10.

The movement of external fixation frame 10 can be controlled by a computer or processor 102 of tool 100. As discussed above, the processor 102 of tool 100 can communicate and interact with host computer C. Host computer C can store and execute an adjustment application to execute a process for controlling the movement of external fixation frame 10 over a predetermined period of time. The memory module MM of host computer C can store the data and/or instructions necessary to run the adjustment application using processor P. The adjustment application may be a web-based application. Suitable applications are described, for example, in U.S. patent application Ser. No. 13/167,101, titled "Methods and Systems for Adjusting an External Fixation Frame," filed Jun. 23, 2011 and U.S. patent application Ser. No. 13/770,056, titled "Software for Use with Deformity Correction," filed Feb. 19, 2013. The disclosures of both of the above applications are hereby incorporated by reference herein.

For purposes of brevity, two brief examples of the use of such an application are described below. It should be understood that there may be a number of other ways in which to create a correction plan for implantation with an external fixation frame, and the descriptions below are merely two examples. Upon initiating the application, a clinician may create a new case and enter patient date, such as name, age, weight, height, or any other information useful to identify and/or treat the patient. The clinician may then import one or more digital representations of the bone to be treated in any suitable format. Suitable formats may include, but are not limited to, Digital Imaging and Communications in Medicine (DICOM) data and digital x-rays images. The clinician may then select the anatomy to be corrected (e.g. right femur or left tibia). The bone deformity to be corrected may then be entered into the application. This deformity definition refers to the anatomical misalignment that the external fixation frame 10 will correct. The deformity definition (also referred as deformity data) may include information about the rotation, translation, angulation, length and vertical translation of the selected bone or anatomy.

The clinician may also enter anatomical limiting factors (ALF) coordinates. ALF refers to factors that may limit the movement of the external fixation frame 10. For example, the ALF may relate to the rate of distraction, as moving portions of the anatomy at too fast or slow a rate during correction may be disadvantageous. Another ALF may be the position of the patient's nerves. During correction of the injured or misaligned bone, stretching of the nerves may occur. Stretching of the nerves should not be too rapid in order to avoid nerve injury. Another ALF can be the patient's skin. If the skin has been compromised, for example in case of an open fracture that part of the skin should not be stretch too rapidly to allow the skin to heal. Up to this point, the two exemplary applications are identical. Following this point, the clinician may choose a pre-operative ("pre-op") or a post-operative ("post-op") mode. The pre-op mode is an optional planning tool designed to virtually test the movement of the external fixation frame 10 without attaching the external fixation frame to a bone. In the post-op mode, the adjustment application runs while the external fixation frame 10 is attached to a bone to correct that bone.

If the clinician selects the pre-op mode of the adjustment application, the application determines all possible strut combinations based on, among other things, the sizes and positions of the rings 14 and 16. The application then allows the clinician to select a strut combination out of all the possible strut combinations. Once the clinician has selected a strut combination, the adjustment application generates a correction plan. The host computer C may then display the correction plan, a simulation of the correction, and a report via any suitable output device, such as a monitor or screen. The report may include, for example, patient data, selected anatomy, correction plan data, inputted deformity definition, inputted ALF coordinates, etc.

If the clinician selects the post-op mode, the application may determine the position of one of the two rings (the "reference" ring) after the clinician enters information regarding the struts and the other of the two rings (the "moving" ring). The information may include the size and position of the reference ring, as well as sizes and orientations of the struts in relation to the reference ring. The adjustment application may determine the position of the moving ring based on, among other things, the inputted digital representations of the bone, anatomy, deformity definition, ALF coordinates and the strut information. Subsequently, the adjustment application generates a correction plan.

Based on at least the initial position of the components of the external fixation frame (and thus the initial position of the deformed bone(s)), the final desired position of the components of the external fixation frame (and thus the final desired position of the corrected bone(s)), and the rate of adjustment of the components, the application may generate a correction plan similar to that illustrated in FIG. 3. The correction plan or "prescription" may be in the form of a table, as shown in FIG. 3 and may include strut or screw identification data (e.g., screw number or letter), amount of rotation (e.g., degrees or radians), length of the strut (e.g. millimeters), direction of rotation (e.g., clockwise or counterclockwise), and frequency of rotation (e.g., in hours and minutes.) Although illustrated in daily increments, the correction plan may span over any desired time and may include, for example, multiple individual adjustments per day. It should be noted that the correction plan illustrated in FIG. 3 is for an external fixation system with six struts connecting a first ring to a second ring.

The correction plan may be referenced during manual adjustment of the external fixation frame by the patient or medical personnel and/or uploaded directly to the tool 100. For examples, the host computer C may be connected directly to tool 100 via bus interface 104. For example, a USB cable may interconnect bus interface 104 and host computer C. Alternatively, communication between host computer C and tool 100 may be established through a closed network or an open network, such and the Internet. If communication is established through a network, the tool 100 may be connected to the network through another computer. In such case, the tool 100 is connected to that computer via bus interface 104. That computer is in turn connected to the network and interacts and communicates with host computer C.

With reference again to FIG. 2, tool 100 may include a processor 102 adapted to execute the correction application stored on memory module 106. Memory module 106 may store the correction plan data used by the correction application. The correction application may be used in conjunction with tool 100 to implement a correction plan algorithm or process.

Figure 4:
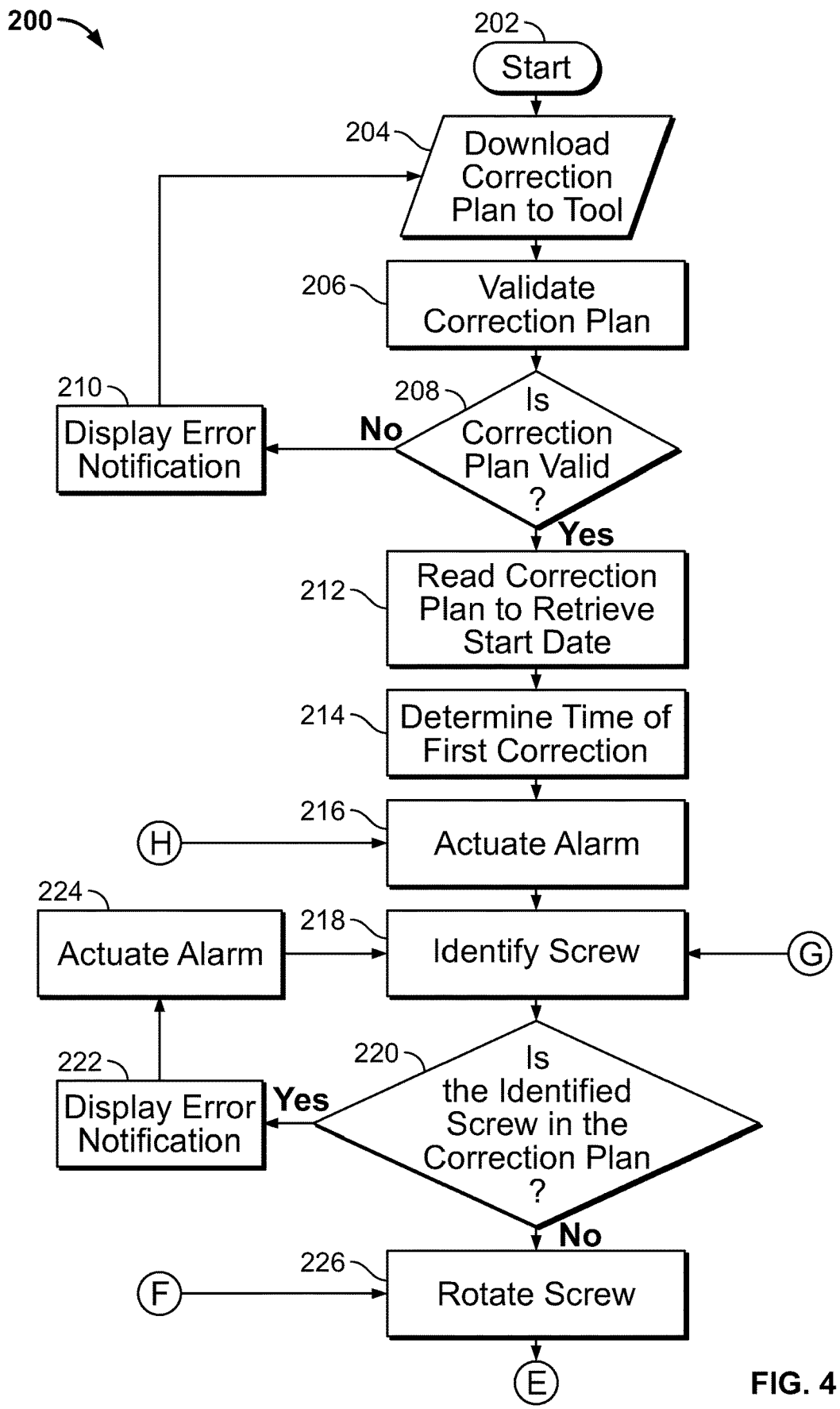
FIGS. 4-5 depict a flowchart illustrating a process for adjusting an external fixation frame according to a correction plan.
Figure 5:
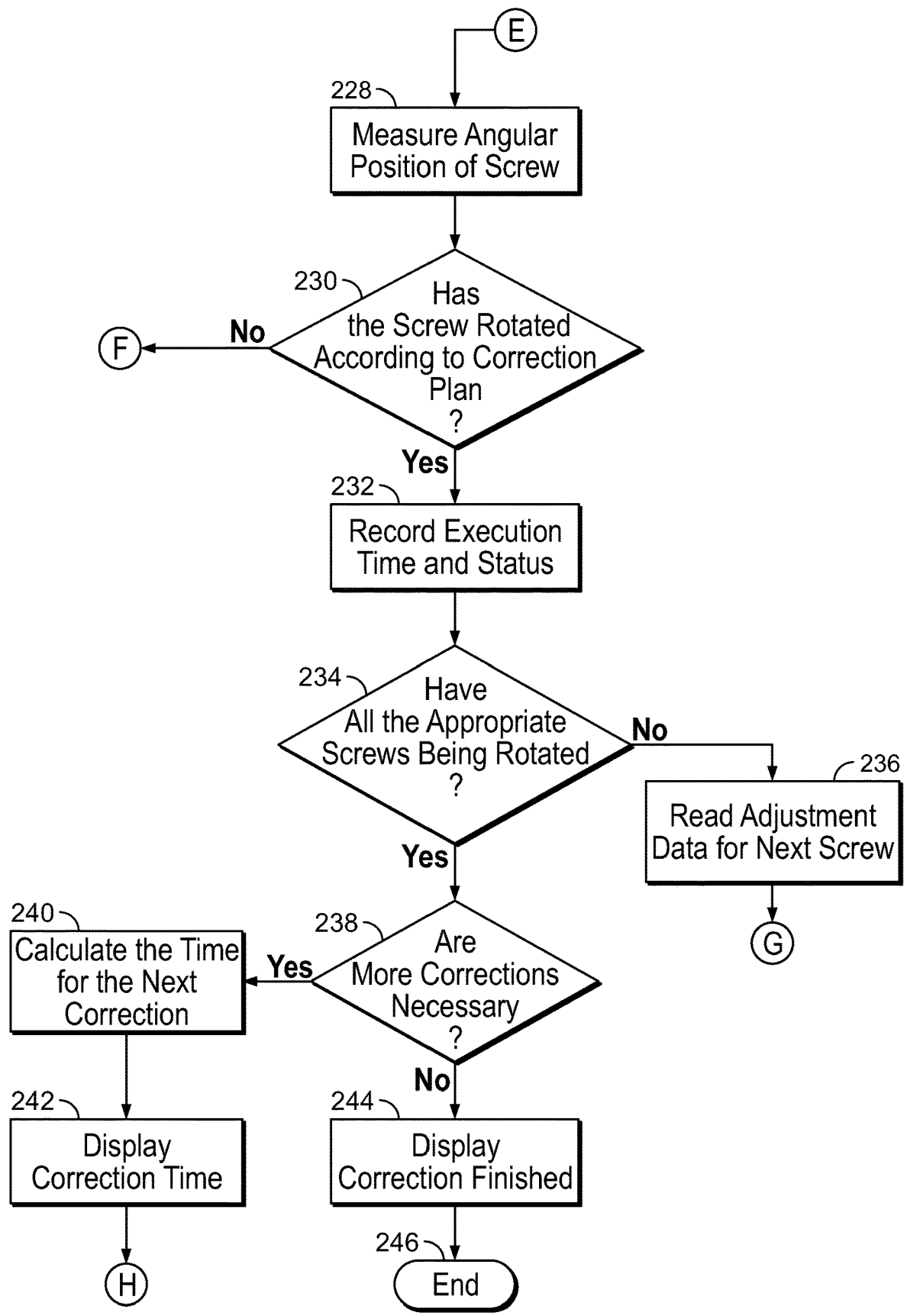

FIGS. 4 and 5 illustrate a flowchart of the correction algorithm or process 200, which starts at block 202. At block 204, correction plan data generated by the adjustment application, as described above, is downloaded to tool 100. The correction plan data is stored on memory module 106 and may include, but is not limited to, screw identification information (e.g., screw number or letter), amount of rotation (e.g., degrees or radians), direction of rotation (e.g., clockwise or counterclockwise), and frequency of rotation (e.g., in hours and minutes). The correction application then validates the correction plan data by, for example, verifying that the data is not corrupted. The clinician is also given the opportunity to validate the correction plan at decision block 208. Accordingly, the correction plan allows the clinician to input whether the correction plan is valid via input device 108 of tool 100. If the correction application or the clinician determines that the correction plan is not valid, the correction application displays an error notification or message, such as "Correction Plan Invalid," at block 210, and then allows the clinician or the patient to input a valid correction plan at block 204. The error notification may be displayed via display unit 110 of tool 100. If the correction plan is valid, the application plan reads the correction plan data stored on memory module 106 to retrieve the start date of the correction plan at block 212.

Based on the retrieved start date, the correction application determines or calculates the precise time (i.e., adjustment time) of the first correction, at block 214. The correction application then actuates alarm 116 to alert the patient that is time to execute a scheduled correction at block 216. Specifically, processor 102 receives a signal from clock 118 at the adjustment time. In response to this signal, the processor 102 sends a signal to alarm 116 to actuate it. At block 218, the patient or clinician may then activate the signal reader 120 of tool 100 to identify the strut or screw to be rotated according to the downloaded correction plan. As discussed above, the signal reader 120 may be an RFID reader. The signal reader 120 is then moved close to a screw 40 or 43 to read signal generated by the identification tags 41 or 44 in each screw 40 or 43. Once the signal reader 120 reads the signal from the identification tags 41 or 44, the processor 102 of tool 100 identifies the screw. The correction application then determines whether the identified screw corresponds to the screw that needs to be rotated according to the downloaded correction plan at decision block 220. If the identified screw does not need to be rotated at that precise moment (i.e., scheduled adjustment time), an error notification is displayed via display unit 110, at block 222, and the alarm 116 is actuated at block 224 to indicate the user that the identified screw does not need to be rotated at the moment. The error notification may include an error message, such as "Invalid Screw." The error message may be displayed at the same time as the alarm is actuated. In response to the error notification, the user may use signal reader 120 to identify the appropriate screw 40 or 43.

If the signal reader 120 identifies the screw 40 that should be rotated according to the correction plan, the user may then securely engage driver 126 to the identified screw 40 or 43. Subsequently, the user activates the motor 124 to rotate the identified screw 40 or 43 at block 226. While the identified screw 40 or 43 rotates, the angular position sensor 125 measures the angular position of the rotating screw at block 228. The angular position sensor 125 sends a signal indicative of the angular position of the identified screw 40 or 43 to the motor controller 122. Based on this signal, the motor controller 122 determines whether the identified screw 40 or 43 has been rotated according to the correction plan at block 230. If the screw has not been completely rotated in accordance with the correction plan, then the motor controller 122 instructs the motor 124 to continue rotating the driver 126 until the identified screw 40 or 43 has been rotated in accordance with the correction plan. Conversely, if the identified screw has been completely rotated according to the correction plan, the motor controller 122 instructs the motor 126 to stop rotating driver 126. The correction application then records when the identified screw was rotated (i.e., execution time) and the status of the rotated screw (e.g., angular position of rotated screw) at block 232. This information may be stored on memory module 106.

The system preferably includes a safety feature to ensure that the adjustment elements are rotated the correct amount when being adjusted by the tool. In rare circumstances, the driver may disengage from the screw head during rotation. In such a case, the system would receive a signal response alerting it that the driver has disengaged from the screw head, allowing the tool to re-engage the adjustment element and to adjust the element the amount it would have been adjusted but for the previous disengagement.

At block 234, the correction application determines whether any other screw needs to be rotated immediately in accordance with the correction plan. If more screws need to be rotated, the processor 102 retrieves and reads the adjustment data for the next screw at block 236. Then, the user may identify the correct screw, at block 218, and rotate said screw as described above. On the other hand, if the correction plan does not provide for immediate rotation of other screws, the correction application determines whether any other corrections are necessary in the future, at decision block 238. If more corrections are necessary, the processor 102 determines or calculates the time for the next correction at block 240. At block 242, the correction time may be displayed through display unit 110. The clock 118 measures time and sends a signal to processor 102 at the next correction time. In response to this signal, the processor 102 actuates alarm 116 at block 216. The correction plan then executes the necessary steps to rotate the appropriate screws in accordance with the correction plan, as discussed in detail above. If no more corrections are necessary, the display unit 110 displays a message or notification indicating that the correction of bone has finished. The message may be, for example, "Correction Finished." The correction application then terminates process 200 at block 246.

Figure 6A:
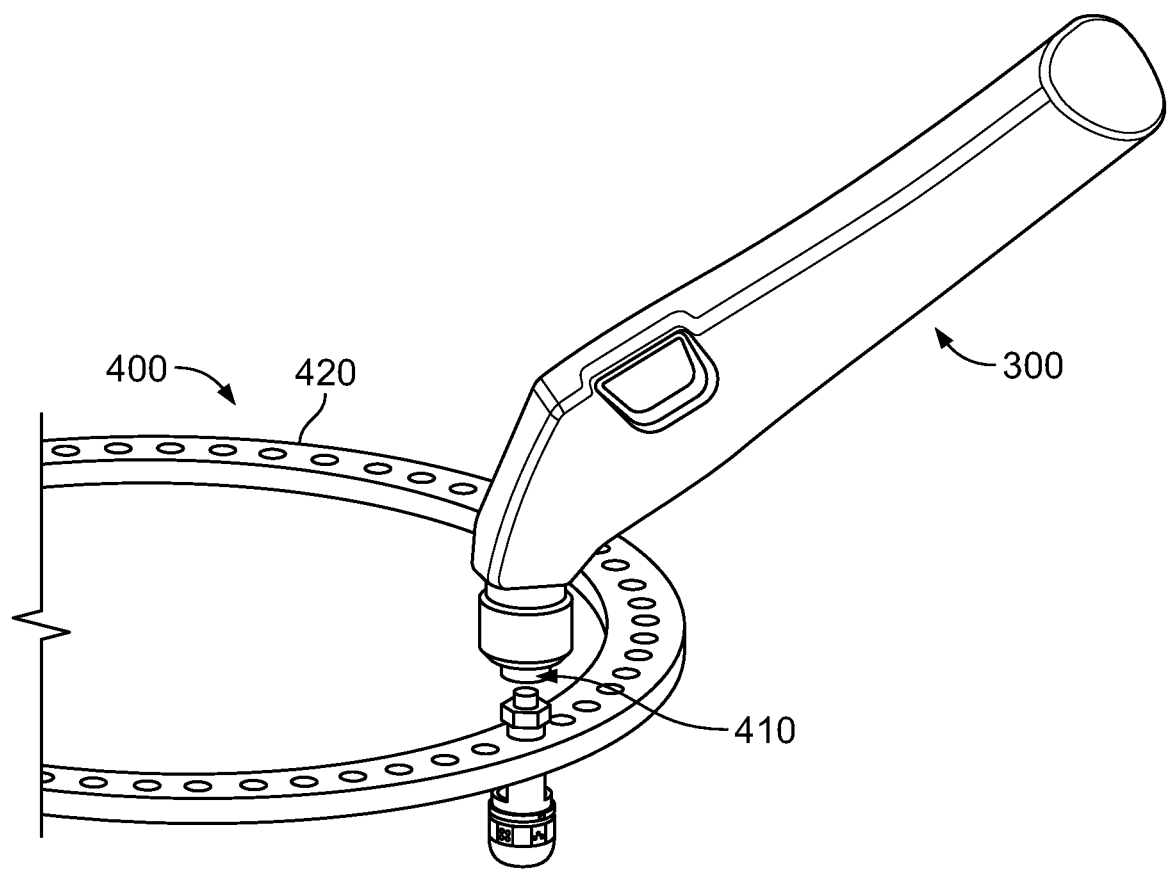
FIG. 6A is a perspective view of a tool for implementing a correction plan coupled to a strut of an external fixation frame.
Figure 6B:
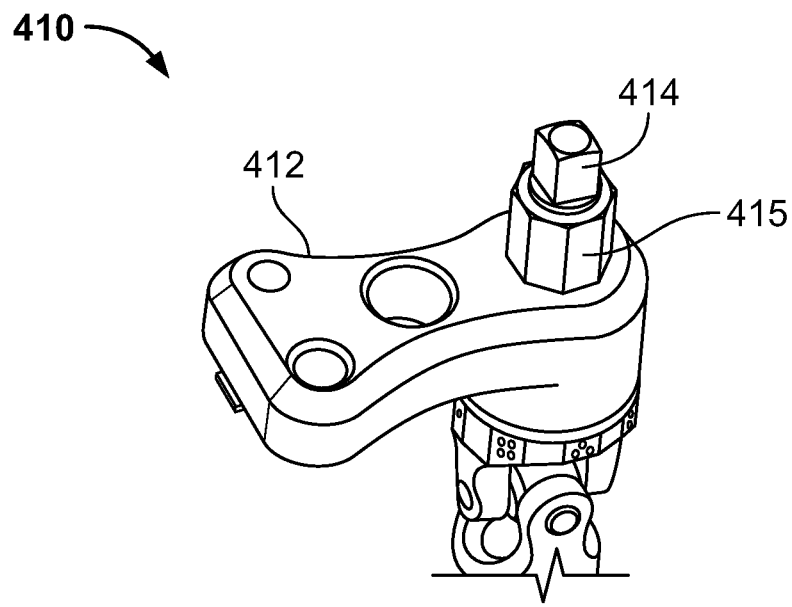
FIG. 6B is an enlarged view of the strut of the external fixation frame to which the tool is connected in FIG. 6A.

Although one particular embodiment of a tool 100 is described above in relation to a particular external fixation frame 10, it should be understood that other embodiments may be suitable to provide similar or enhanced functionality. For example, FIG. 6A illustrates a tool 300 engaged with a portion of an external fixation frame 400. It should be understood that tool 300 may provide similar functionality for any device with components that are to be rotated or otherwise actuated with precision. In this particular embodiment, tool 300 is engaged with a strut 410 connected to a first ring 420 of external fixation frame 400. It should be understood that external fixation frame 400 would generally include one or more additional rings (not shown) that may take any suitable shape, including the circular shape of first ring 420. Further, external fixation frame 400 would generally include three or more struts 410 connecting the two or more rings as appropriate. Various types of struts 410 may be suitable for use with external fixation frame 400, and struts 410 may be connected to the rings in a variety of ways. For example, as illustrated in FIG. 6B, strut 410 may include a flange 412 configured to be connected to first ring 420 through one or more apertures. Strut 410 may include a head 414 at one end thereof, wherein rotation of the head 414 causes a change in the length of strut 410, and thus causes a change in the position of first ring 420 in relation to the other ring(s) to which strut 410 is coupled. One suitable mechanism for causing the change in length of strut 410 via rotation of head 414 is described in greater detail in U.S. Patent Publication No. 2012/0041439, the disclosure of which is hereby incorporated by reference herein. With such a mechanism, head 414 may rotate with respect to strut connector 415, which, along with flange 412, is rotationally fixed with respect to the ring 420 to which the strut 410 is coupled. Strut connector 415 may have a square, hexagonal, octagonal, or other suitable shape.

Figure 7A:
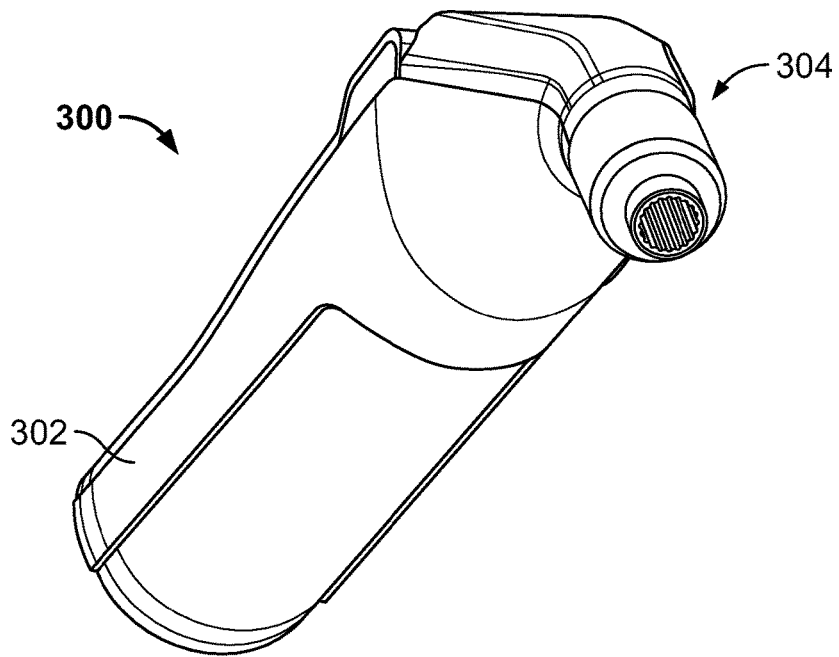
FIG. 7A is a perspective view of the tool of FIG. 6A.
Figure 7B:
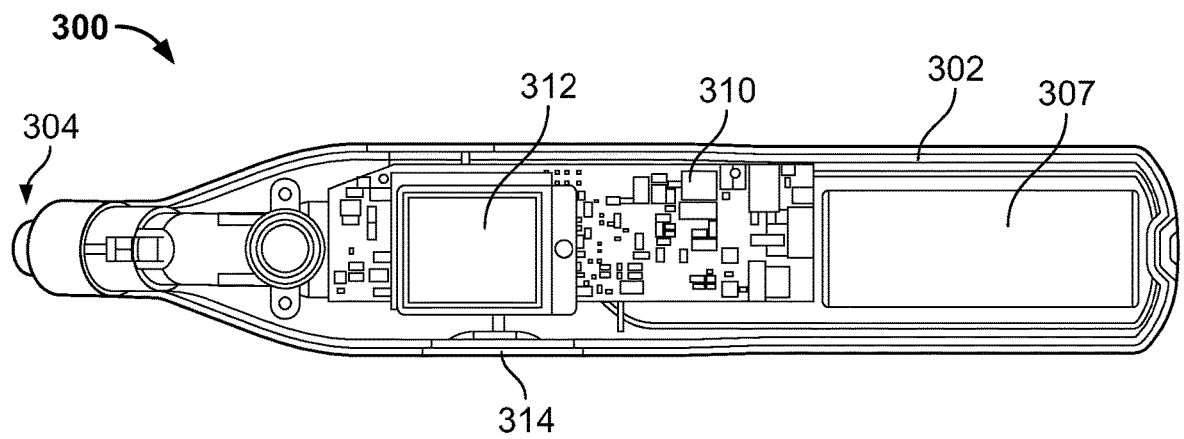
FIGS. 7B-C are top and side views of the tool of FIG. 7A shown in partial transparency.
Figure 7C:
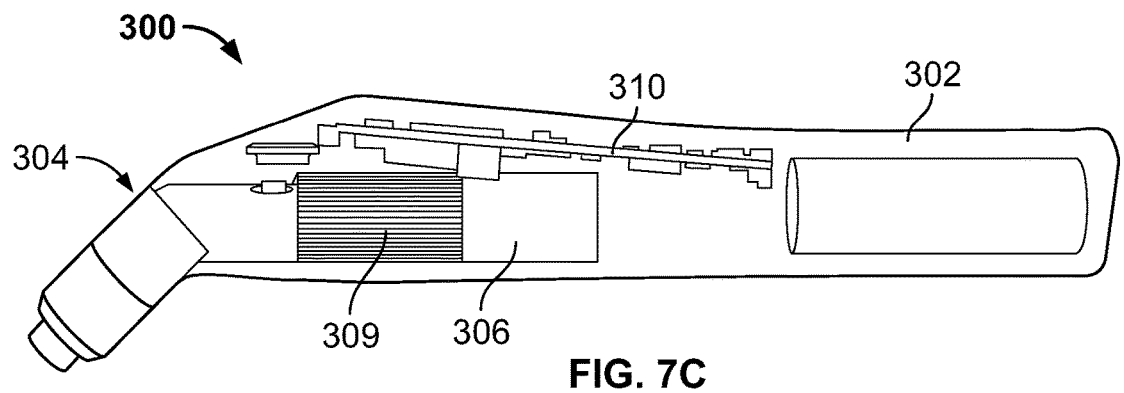
Figure 7D:
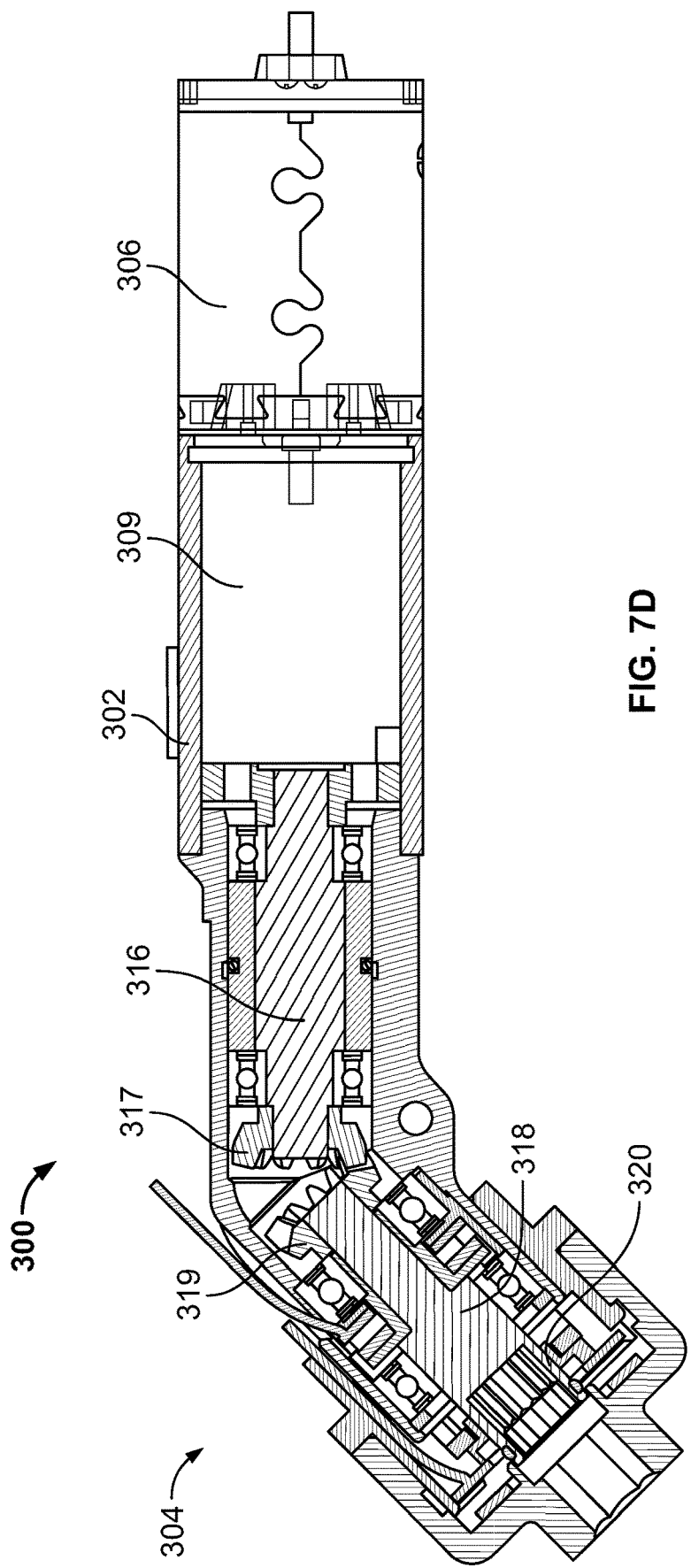
FIG. 7D is a sectional view of the tool of FIG. 7A.

Tool 300 is illustrated in greater detail in FIGS. 7A-D. Tool 300 may include a housing having a handle portion 302 and an actuation portion 304. The handle portion 302 may be at a generally opposite end of the housing than the actuation portion. The handle portion 302 may be configured to be gripped by a user, while the actuation portion 304, or a portion thereof, may be adapted to engage one or more struts, such as strut 410, of an external fixation frame, such as external fixation frame 400. A motor 306 may be included in the housing. The motor 306 may be operatively coupled to one or more gear mechanisms, such as planetary reduction gearbox 309. The motor 306, as well as other components of tool 300, may be powered by one or more internal batteries 307 within the housing. In the case that there are no internal batteries configured to provide power to the motor, the motor 306 may operate on power supplied through an external power source, for example via a wired connection. Tool 300 may also connect to a computer or other external device, for example via a wired or wireless connection, so that the tool 300 may receive or transmit data relating to operation of the tool, or any other relevant data. The tool 300 may additionally or alternatively be supplied with any suitable wireless transmitter and/or receiver for the transmission and reception of such data. As best seen in FIGS. 7B-C, the tool 300 may include various electronic components 310, for example including a processor and memory components. In addition, tool 300 may include a display 312 for displaying relevant information to a user. One or more input components, such as a button (not illustrated), may be positioned adjacent the display to allow the user to scroll through different screens on the display or to otherwise input data or commands. One or more speakers may also be included with tool 300, for example to provide audible alarms or to provide for other sounds.

In use, when tool 300 is connected to a power source and/or has a sufficiently charged internal battery, a user may actuate the motor 306, for example by depressing an actuation button 314 on the tool 300. Upon actuation, motor 306 causes rotation of a driving element. For example, the motor 306 may cause rotation of a first output shaft 316, which rotation may be transmitted to a second output shaft 318 via any suitable gear assembly, such as bevel gears 317 and 319 of first and second output shafts 316, 318, respectively. A distal end of second output shaft 318 may include a connector 320 having a shape complementary to the shape of the head 414 of strut 410, such as a square or hexagonal shape, such that rotation of second output shaft 318 is transmitted to head 414 of strut 410 when the two are connected.

Actuation portion 304 of tool 300, coupled to strut 410, is illustrated in greater detail in FIG. 8A. FIG. 8B shows the actuation portion 304 of tool 300 isolated. After coupling connector 320 of second output shaft 318 to head 414 of strut 410, the tool 300 may determine whether the tool 300 is coupled to the correct strut 410. For example, strut 410 may include an identification tag, such as an RFID tag 416, within the head 414 of the strut 410. The tool 300 may include an identification tag reader, such as an RFID antenna 328, to read data on the identification tag. The data may be, for example, a unique code. The RFID tag 416 and RFID antenna 328 may be configured such that the antenna 328 only recognizes the tag 416 when the two are in close proximity, for example between about 1 mm and about 2 mm. With this configuration, the tool 300 may be configured to restrict operation of the motor 306 if the tool 300 is not engaged with a strut 410. Once the tool 300 is properly engaged with the head 414 of a strut 410, the RFID antenna 326 and RFID tag 416 may be in close enough proximity for the antenna 326 to recognize the particular strut 410. Based on instructions stored in the electronic circuitry 310 of the tool 300, the motor 306 may be actuated by the user to rotate strut 410 no more than a prescribed amount. For example, if an instruction schedule calls for a single revolution of strut 410 at a particular time, the motor 306 may be actuated only once the antenna 328 recognizes the particular strut 410 via the RFID tag 416, and actuation of motor 306 may be restricted once again after the full amount of prescribed rotation of strut 410 is complete.

In the illustrated embodiment, actuation portion 304 includes a proximal housing 322, an intermediate housing 324, and a distal housing 326. When tool 300 is connected to strut 410, a distal portion of distal housing 326 is coupled to the connector 415 of strut 410. The distal portion of distal housing 326 may have a shape complementary to the shape of connector 415 of strut 410, preferably with at least one edge so that when tool 300 is coupled to strut 410, distal housing 326 is rotationally fixed in relation to connector 415. On the other hand, when tool 300 is coupled to strut 410, proximal housing 322 and intermediate housing 324 are both rotatable with respect to connector 415. Actuation portion 304 may also include an internal housing 323 which may be fixed to intermediate housing 324. Upon actuation of the motor 306, rotation is transmitted to second output shaft 318, as described above. Rotation of second output shaft 318 due to the actuation of motor 306 only will cause little or no rotation of intermediate housing 324. The rotation of second output shaft 318 relative to inner housing 323 may be facilitated by one or more bearings B of any suitable type, such as ball bearings. Relative motion between second output shaft 318 and internal housing 323 may be tracked with a rotary encoder. For example, second output shaft 318 may include a flange 330 fixed thereto, with an electromagnetic code wheel 332 fixed to the flange 330. A pulse pattern receiver 334, such as an encoder chip on a printed circuit board, may be operatively fixed to the internal housing 323. With the above described configuration, as the motor 306 is actuated and torque is transmitted to second output shaft 318, the second output shaft 318 including code wheel 332 rotates relative to internal housing 323, including pulse pattern receiver 334. Thus, as second output shaft 318 causes strut 410 to rotate, the rotation is tracked by the rotary encoder to ensure that the strut 410 is rotated as prescribed, and once the prescribed rotation limit is reached, the motor 306 may be instructed to stop, even if the user is still depressing the actuation button 314.

One potential issue with the configuration described above is that a user may intentionally or unintentionally manually rotate the tool 300 before, after, or during actuation of motor 306. If such manual rotation of tool 300 occurs, the output shaft 318 will rotate and cause strut 410 to rotate, but internal housing 323 will also rotate in sync with the output shaft 318. Because such manual rotation causes simultaneous rotation of the output shaft 318 and the internal housing 323, both the code wheel 332 and pulse pattern receiver 334 will rotate simultaneously. Further, since the rotary encoder system tracks only relative rotation between the code wheel 332 and pulse pattern receiver 334, rotation of the head 414 of strut 410 due to manual rotation of the tool 300 will not be detected, despite the fact that the manual rotation of the tool 300 is resulting in rotation of the head 414 of strut 410. To account for the above scenario, a second rotary encoder may be included with actuation portion 304 of tool 300. For example, a second rotary encoder may include a second code wheel 336 fixed to the distal housing 326 and a second pulse pattern receiver 338 fixed to the intermediate housing 324 adjacent the second code wheel 336. Rotation of output shaft 318 due to the actuation of motor 306 is not captured by the second rotary encoder because distal housing 326 is always rotationally fixed with respect to the connector 415 of strut 410, and actuation of motor 306 does not cause rotation of intermediate housing 324. However, manual rotation of tool 300 causes rotation of inner housing 323 which is fixed to intermediate housing 324, thus intermediate housing 324 rotates with respect to distal housing 326 upon manual rotation of the tool 300.

Thus, the first rotary encoder may track rotation of the head 414 of strut 410 due to the actuation of motor 306, while the second rotary encoder may track rotation of the head 414 of strut 410 due to manual rotation of tool 300. The tracked values of rotation of the first and second rotary encoders may be added (or subtracted, depending on the directionality of rotation) to precisely determine how far the head 414 has rotated after tool 300 is coupled to strut 410. This precise value may be compared to the prescribed rotational limit provided for the particular strut 410 for the particular time, so that a user does not over rotate strut 410. Once the rotation limit is met, as noted above, the motor 306 is instructed to restrict any further rotation. An alarm, such as an audible alarm, may be activated as well to alert the use that the rotational limit has been met. This alarm may be useful, for example, because even with a disengaged motor 306, manual rotation of the tool 300 to cause rotation of the head 414 of strut 410 is possible. The alarm may alert the user to disengage the tool 300 from the strut 410, to eliminate the possibility of further unintentional manual rotation of the strut 410. However, if any manual rotation occurs after disengagement of the motor 306, that manual rotation may be tracked via the second rotary encoder and taken into account, for example by being added to or subtracted from the next scheduled rotation.

It should be understood that tool 300 may be provided in another embodiment without the motor 306. In such an embodiment, all rotation is manual and may be tracked via the second rotary encoder, with the alarm indicating whether or not rotational limit has been met. In this embodiment, the first rotary encoder may be unnecessary, and the shape of the tool may take other more convenient forms for manual rotation, such as a non-angled body with a handle for facilitating a user griping and rotating the tool manually. Similar to the embodiment described directly above, the manual version of tool 300 may also include a display, such as an LCD display, and alarm features, including speakers.

Figure 9B:
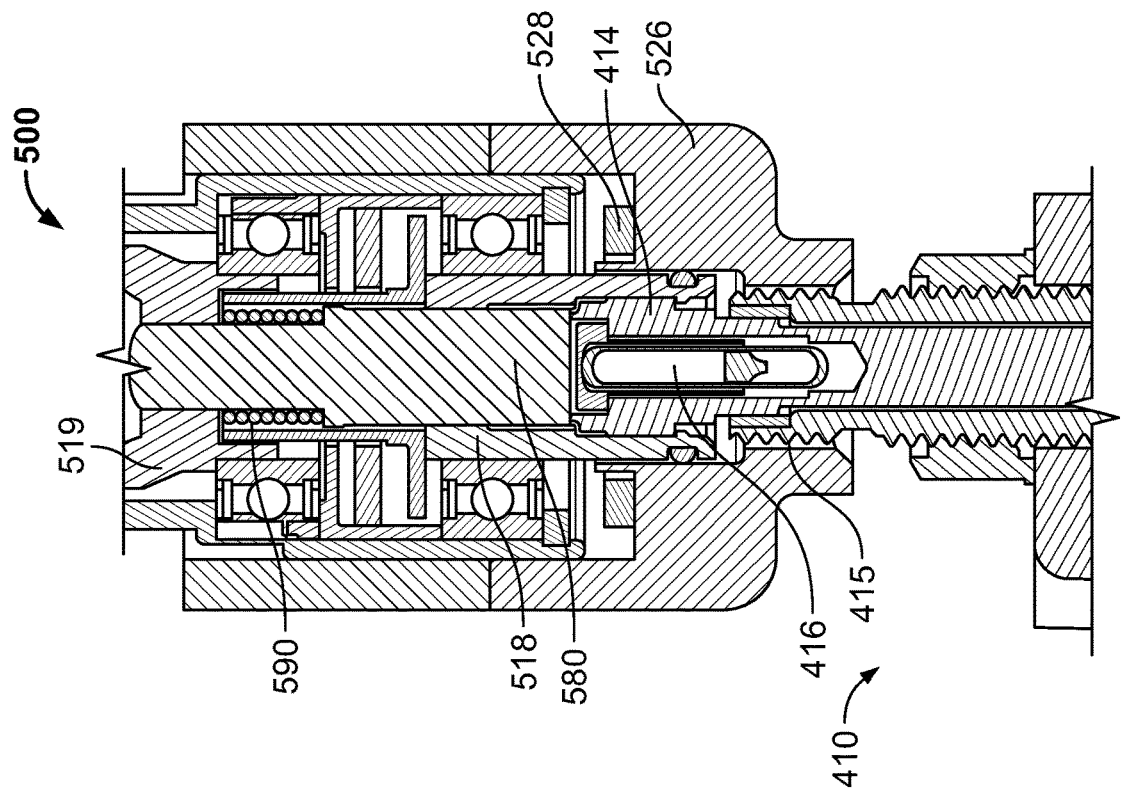
FIG. 9B is a sectional view of the distal end of the tool of FIG. 9A engaged with the strut of FIG. 6B in a final engagement position.
Figure 9A:
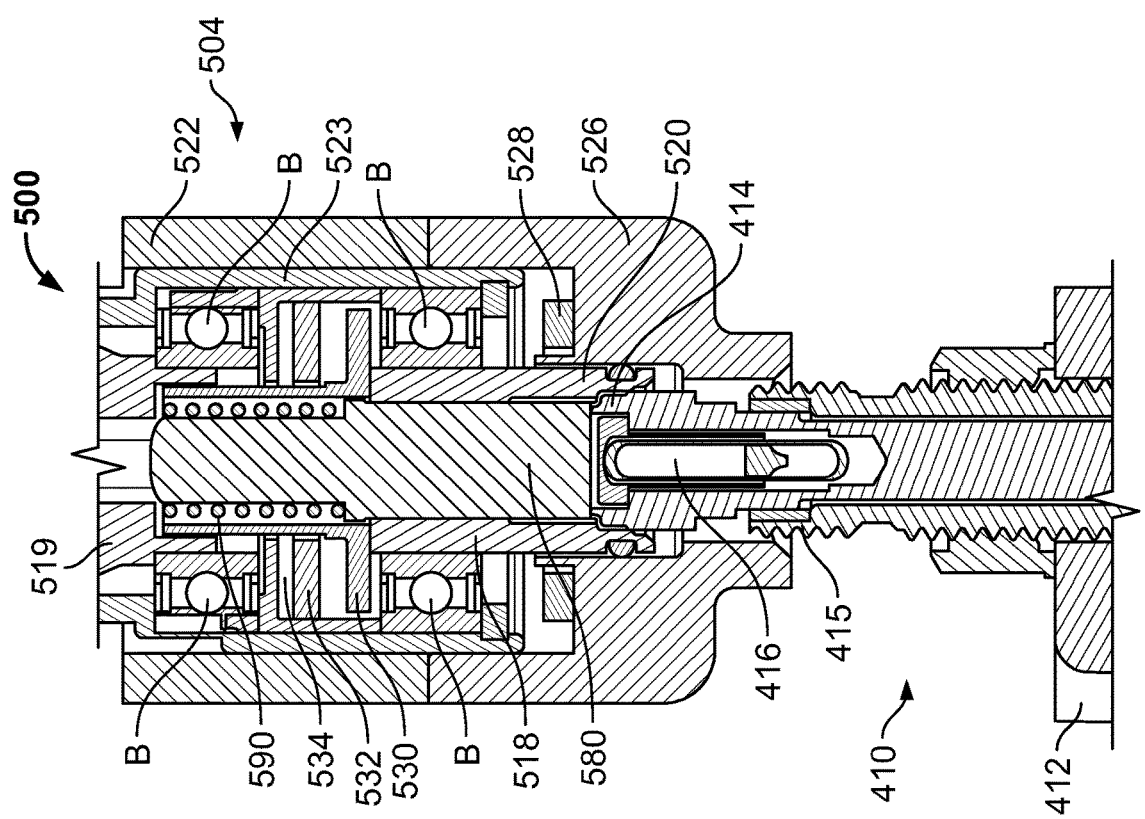
FIG. 9A is a sectional view of a distal end of a tool according to another aspect of the disclosure engaged to the strut of FIG. 6B in an initial engagement position.
Figure 10D:
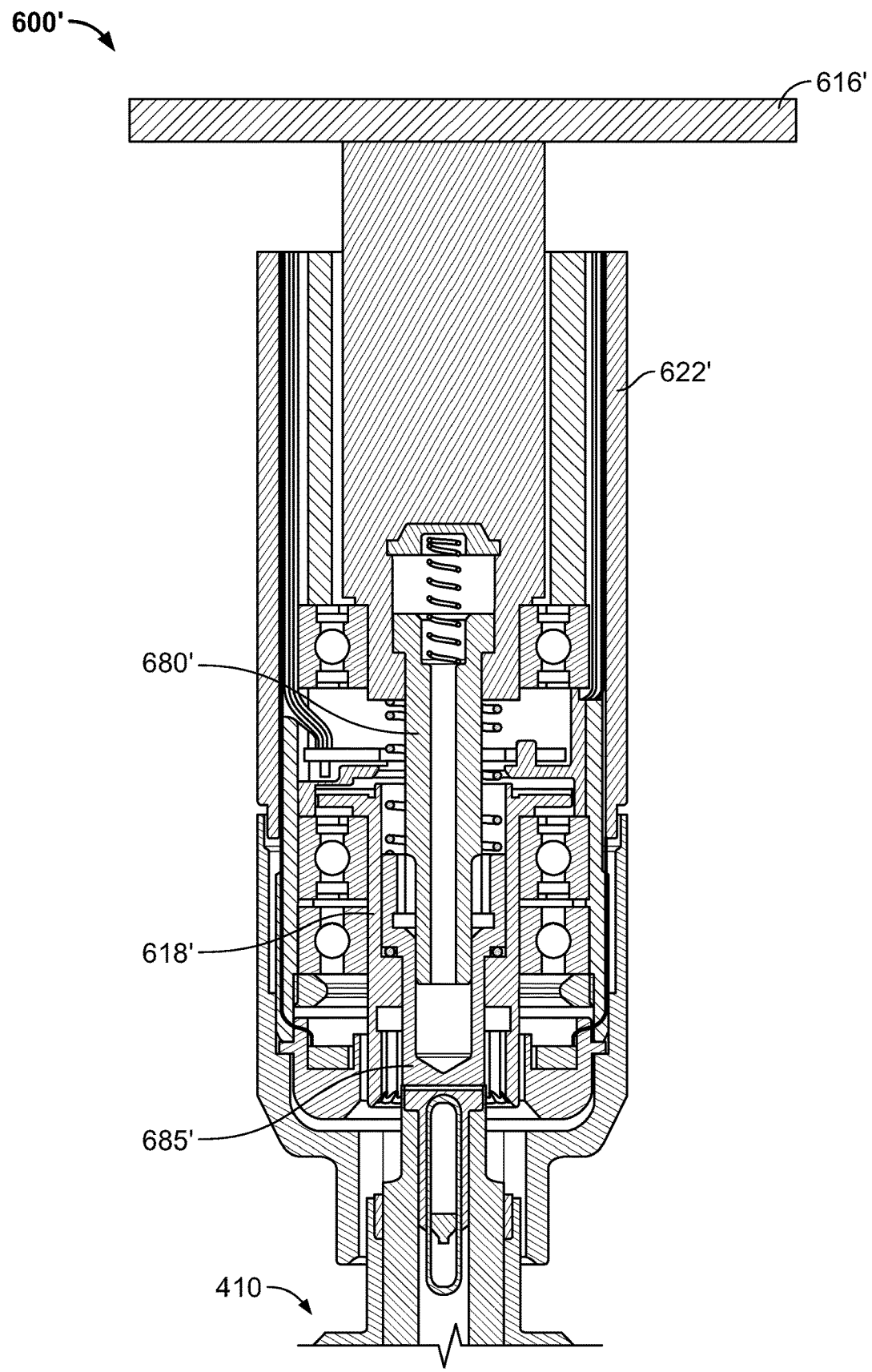
FIG. 10D is a sectional view of a manual version of the tool of FIG. 10A in an initial engagement position.

Another embodiment of a tool 500 is illustrated in FIGS. 9A-B. Tool 500 is similar to tool 300 in a number of ways, but includes different features that may help further ensure that tool 500 cannot be actuated before engaging strut 410, and further to help ensure that tool 500 remains engaged to strut 410 during operation. Tool 500 may include a housing similar to tool 300, with a motor, display, and electronic components described above in connection to tool 300. Only an actuation portion 504 of tool 500 is illustrated in FIGS. 9A-B, in initial and final stages of engagement, respectively.

In the illustrated embodiment, actuation portion 504 may include a proximal housing 522 and a distal housing 526. Tool 500 may include a motor attached to a first output shaft with a first gear, and a second output shaft 518 connected to a second gear 519, the second gear 519 configured to interact with the first gear (not shown) in a similar fashion as described in connection with tool 300. Second output shaft 518 may include a hollow portion with a sliding member 580 positioned therein, the sliding member 580 having a relatively large diameter distal portion and a relatively small diameter proximal portion. A spring member 590 may be positioned around the proximal portion of sliding member 580, with one end of the spring member 590 abutting the distal portion of the sliding member 580 and the other end of the spring member 590 abutting the second gear 519. The second gear 519 may include a recess therein, for example having a square or hexagon shape, into which a portion of the proximal portion of sliding member 580 may enter.

Tool 500 may include an internal housing 523 which may rotate with respect to proximal case housing 522. Distal housing 526 may have be rotationally fixed with respect to connector 415 of strut 410 in a similar fashion described in connection with tool 300. A flange 530 may be coupled to second output shaft 518. A first rotary encoder may be positioned with respect to flange 530 and internal housing 523 to track rotation of second output shaft 518 with respect to internal housing 523, similar to that described above. For example, the first rotary encoder may include a first code wheel 532 coupled to the flange 530 and a first pulse pattern receiver 534 coupled to the internal housing 523. The first rotary encoder may work in an identical manner to the first rotary encoder described in connection with tool 300.

Also similar to tool 300, tool 500 may include an identification tag reader, such as a RFID antenna 528, coupled to distal housing 526. Upon initial engagement of tool 500 with strut 410, as illustrated in FIG. 9A, RFID antenna 528 and RFID tag 416 are not aligned. Rather, upon initial engagement of tool 500 with strut 410, a distal end of sliding member 580 contacts head 414 of strut 410 to resist such alignment between the RFID antenna 528 and RFID tag 416. Similarly, a connector portion 520 of second output shaft 518 is less than fully engaged with head 414 of strut 410, and the distal end of housing 526 is less than fully engaged with the connector 415 of strut 410. In this initial engagement position, the motor of the tool 500 is restricted from being actuated as the RFID antenna 528 is not in a position to recognize RFID tag 416 of strut 410. In order to align the RFID antenna 528 and RFID tag 416, the user may push tool 500 downward into the final engagement position shown in FIG. 9B. As shown in FIG. 9B, the force provided by the user causes spring member 590 to compress as a proximal portion of slide member 580 slides into the recess in second gear 519. In this final engagement position, the distal end of distal housing 526 is fully engaged with connector 415 of strut 410. Similarly, the connector portion 520 of second output shaft 518 is fully engaged with head 414 of strut 410. Upon recognition of RFID tag 416 by RFID antenna 528, a signal may be sent to the electronic circuitry to allow the motor to be activated. With this configuration, the likelihood of accidentally actuating the motor of tool 500 prior to full engagement of the tool 500 with the strut 410 is minimized, for example, because the user may need to intentionally and forcefully press the tool 500 onto the strut 410 before actuation of the motor is possible.

Distal housing 526 may be fixed to proximal housing 522, for example by, welding, gluing or other suitable means. In addition, internal housing 523 may be fixed to distal housing 526 with similar means. In this configuration, since distal housing 526 is rotationally fixed to connector 415 of strut 410 when in the fully engaged position, manual rotation of the head 414 of strut 410, whether intentional or unintentional, is prevented. As such, no secondary rotary encoder is needed to track such movements, since they are restricted by the physical configuration of tool 500.

It should be noted that various modifications may be made to tool 500, including reconfiguring the tool as a manual tool. For example, in FIG. 9C, tool 500', a manual version of tool 500, is shown. Most components of tool 500' are identical to those of tool 500, with a few exceptions to provide for manual operation. For example, the motor of tool 500 may be removed in manual tool 500'. Rather than a motor driving a first shaft that interacts with a second gear 519 that interacts with a second output shaft 518, manual tool 500' includes a handle 516' that extends out of the housing and which may be grasped by the user. The handle 516' extends through tool 500' and a distal end of handle 516' includes a recess similar or identical to the recess in second gear 519 of tool 500. With this configuration, the user may grasp the outer housing 522' of manual tool 500' with one hand, and place it proximate strut 410. In the disengaged position shown in FIG. 9C, rotation of handle 516' will not drive the second output shaft 518' because the proximal end of the sliding member 580' is not within the recess of the distal end of handle 516'. Similar to the automatic tool 500, the user may push manual tool 500' down onto strut 410 to engage the manual tool 500' with the strut 410. Once engaged, the user may rotate handle 516' with the other hand to rotate the head 414 of strut 410. Although the general principles of action are very similar between automatic tool 500 and manual tool 500', manual tool 500' may provide significant cost savings over the use of automatic tool 500, without loss of functions such as tracking rotation and helping ensure engagement of the tool to the correct strut 410.

Another embodiment of a tool 600 is illustrated in FIGS. 10A-C. Tool 600 is similar to tool 500 in a number of ways, but includes different features that may help further ensure that tool 600 cannot be actuated before engaging strut 410, and further to help ensure that tool 600 remains engaged to strut 410 during operation. Tool 600 may include a housing similar to tools 300 and 500, with a motor, display, and electronic components described above in connection to tool 300. Only an actuation portion 604 of tool 600 is illustrated in FIGS. 10A-C, with FIGS. 10B-C showing tool 600 in initial and final stages of engagement, respectively.

In the illustrated embodiment, actuation portion 604 may include a proximal case housing 622, shown in FIGS. 10B-C, and a distal housing 626. Tool 600 may include a motor attached to a first output shaft 616 with a first gear 617, and a second output shaft 618 operatively connected to a second gear 619, the second gear 619 configured to interact with the first gear in a similar fashion as described in connection with tool 300. Second output shaft 618 may include a hollow portion with a sliding member 680 and a guide member 685 positioned therein, a distal end of the sliding member 680 being configured to slide into guide member 685. A proximal end of slide member 680 may be positioned within a recess in second gear 619. The guide member 685, sliding member 680, and internal recess in second gear 619 may all have corresponding shapes, such square, hexagonal, octagonal, or the like, to facilitate transmission of torque between the components, as is described in greater detail below. A first spring member 690 may be positioned around sliding member 680, with one end of the first spring member 690 abutting a distal end of the second gear 619 and the other end of the spring member 690 abutting an internal flange of the second output shaft 618. A second spring member 692 may be positioned within the recess of second gear 619, with a first end of the second spring member 692 abutting a proximal end of the sliding member 680 and the other end of the second spring member 692 abutting a cap 694 fixed to the second gear 619.

Tool 600 may include an internal housing 623 rotationally fixed to proximal housing 622 and distal housing 626. A flange 630 may be coupled to second output shaft 618. A first rotary encoder may be positioned with respect to flange 630 and internal housing 623 to track rotation of second output shaft 618 with respect to internal housing 623, similar to that described above. For example, the first rotary encoder may include a first code wheel 632 coupled to the flange 630 and a first pulse pattern receiver 634 coupled to the internal housing 623. The first rotary encoder may work in an identical manner to the first rotary encoder described in connection with tool 300.

Also similar to tool 300, tool 600 may include an identification tag reader, such as a RFID antenna 628, coupled to distal housing 626. Upon initial engagement of tool 600 with strut 410, as illustrated in FIG. 10B, RFID antenna 628 and RFID tag 416 are not aligned. Rather, upon initial engagement of tool 600 with strut 410, a distal end of guide member 685 contacts head 414 of strut 410 to resist such alignment between the RFID antenna 628 and RFID tag 416. Similarly, a connector portion 620 of second output shaft 618 is not fully engaged with head 414 of strut 410, and the distal end of distal housing 626 is less than fully engaged with the connector 415 of strut 410. In this initial engagement position, the motor of the tool 600 is restricted from being actuated as the RFID antenna 628 is not in a position to recognize RFID tag 416 of strut 410. It should be understood that the connector portion 620 of second output shaft 618 may include a shape complementary to the head 414 of strut 410 that permits transmission of torque—for example a square, hexagonal, or octagonal shape. Similarly, as in tool 300 and 400, the distal end of distal housing 626 may include a similar complementary shape to the connector 415 of strut 410 to prevent rotation of the distal housing 626 with respect to the connector 415. Preferably, as with the embodiments described above, strut 410 includes a fixed connection to ring 420 of external fixator 400, so that connector 415 is unable to rotate with respect to the head 414 of strut 410.

In order to align the RFID antenna 628 and RFID tag 416, the user may push tool 600 downward into the final engagement position shown in FIG. 10C. The force provided by the user causes second spring member 692 to compress first as a proximal portion of slide member 680 slides into the recess in second gear 619. As the user continues to apply force after second spring member 692 is compressed, first spring member 690 compresses and the distal end of slide member 680 slides distally into guide member 685. As the first and second spring members 690, 692 are compressing, the distal ends of second output shaft 618 and distal housing 626 slide distally over an end of the strut 410 to the final engagement position. In this final engagement position, the distal end of distal housing 626 is fully engaged with connector 415 of strut 410. Similarly, the connector portion 620 of second output shaft 618 is fully engaged with head 414 of strut 410. Upon recognition of RFID tag 416 by RFID antenna 628, a signal may be sent to the electronic circuitry to allow the motor to be activated. If the motor starts to cause rotation of the slide member 680 before the edges of the distal end of slide member 680 are perfectly aligned with corresponding inner edges of guide member 685 (e.g. hex to hex or octagon to octagon alignment), force provided by second spring 692 may help drive slide member 680 into proper engagement with guide member 685. With this configuration, similar to tool 500, the likelihood of accidentally actuating the motor of tool 600 prior to full engagement of the tool 600 with the strut 410 is minimized, for example, because the user may need to intentionally and forcefully press the tool 600 onto the strut 410 before actuation of the motor is possible. Similarly, manual rotation is effectively impossible in this embodiment because the distal end of distal housing 626 is rotationally fixed to connector 415 of strut 410, and the fixed connection between connector 415 and ring 420 prevents rotation of connector 415. That, in combination with the rotationally fixed connection between distal housing 626, internal housing 623, and proximal housing 622, prevents intentional or unintentional manual rotation of the head 414 of strut 410.

As with tool 500, tool 600 may be reconfigured to work as a manual tool. For example, in FIG. 10D, tool 600', a manual version of tool 600, is shown. Most components of tool 600' are identical to those of tool 600, with a few exceptions to provide for manual operation. For example, the motor of tool 600 may be removed in manual tool 600'. Rather than a motor driving a first shaft that interacts with a second gear 619 that interacts with a second output shaft 618, manual tool 600' includes a handle 616' that extends out of the housing and which may be grasped by the user. The handle 616' extends through tool 600' and a distal end of handle 616' includes a recess similar or identical to the recess in second gear 619 of tool 600. With this configuration, the user may grasp the outer housing 622' of manual tool 600' with one hand, and place it proximate strut 410. In the disengaged position shown in FIG. 10D, rotation of handle 616' will not drive the second output shaft 618' because the distal end of the sliding member 680' is not engaged with guide member 685'. Similar to the automatic tool 600, the user may push manual tool 600' down onto strut 410 to engage the manual tool 600' with the strut 410. Once engaged, the user may rotate handle 616' with the other hand to rotate the head 414 of strut 410. Although the general principles of action are very similar between automatic tool 600 and manual tool 600', manual tool 600' may provide significant cost savings over the use of automatic tool 600, without loss of functions such as tracking rotation and helping ensure engagement of the tool to the correct strut 410.

For all of the embodiments described above, it should be understood that other mechanisms of identifying engagement of the tool with a particular strut may be used other than RFID including, for example, optical RFID, bar codes, and the like. In addition, mechanical means may be used to identify engagement of the tool with a particular strut. For example, in an external fixation system with three struts (or more or fewer struts) to be adjusted, each strut may include a head with a different engagement shape including, for example, square, pentagon, and hexagon. The tool may include a group of second output shafts with end connectors (or a single second output shaft with different connectors) having corresponding shapes. The user may attach the square connector to the tool, which the tool may recognize. Since the square connector only fits over the strut with the square head, the motor may be instructed to only allow the particular rotation of the square-headed strut according to the inputted correction schedule. Once adjustment of the square-headed strut is complete, the user may switch out the connector of the tool for the hexagon connector and adjust the hexagon-headed strut. The process may be continued with the remaining struts until each adjustment for a particular time period of the schedule is completed. When the time comes for the next adjustment the process may be repeated. Although discussed in terms of rotating struts of external fixators, it should be understood that the concepts provided herein apply to rotation of any rotatable structure where precision is desired.

Similarly, although particular rotary encoders are disclosed above, other means may be used to track movement of the struts 410 of the external fixation frame 400. For example, accelerometers or gyrometers may provide suitable functionality to track the progress of the adjustment of external fixation frame 400 during adjustment periods of the correction schedule.

Figure 11A:
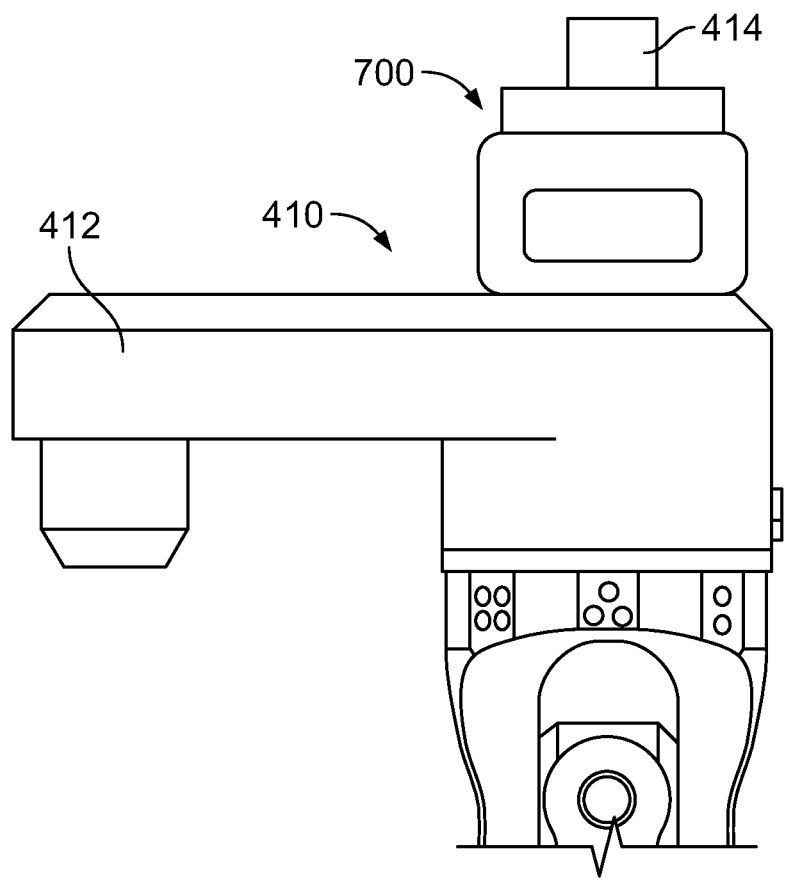
FIG. 11A is a side view of a correction indicator coupled to the strut of FIG. 6B.
Figure 11B:
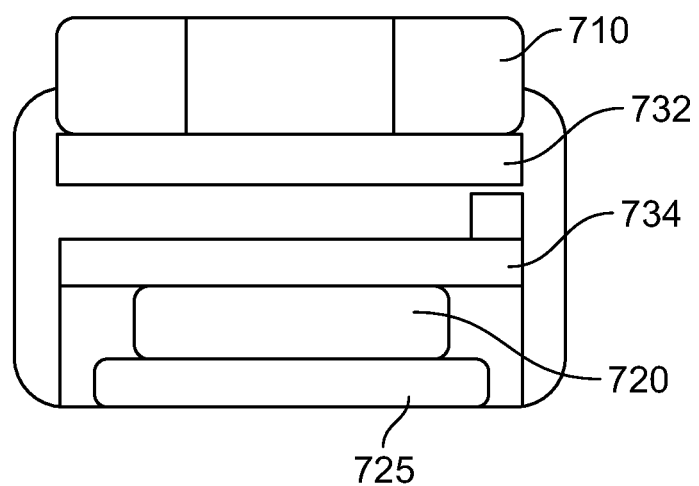
FIG. 11B is an isolated sectional view of the correction indicator of FIG. 11A.

Other systems may be used in addition or alternatively to the tools described above to facilitate accurate adjustment of struts 410 of an external fixation frame 400 by a user. For example, referring to FIGS. 11A-B, strut 410 is illustrated with a correction indicator 700 mounted on the strut 410. The correction indicator 700 may include a guide bushing 710, a display 720, a battery 725, a code wheel 732, and a pulse pattern receiver and electronic board 734. The guide bushing 710 and code wheel 732 may be fixed to one another and fixed to the head 414 of strut 410. The guide bushing 710 may include a recess through which head 414 of strut 410 extends. Because of the fixed relationship between the guide bushing 710, code wheel 732, and head 414, as a user rotates head 414 to change the length of strut 410, guide bushing 710 and code wheel 732 rotate in sync with head 414. Pulse pattern receiver 734, on the other hand, may be fixed to a non-rotating portion of strut 410, such as connector 415 (see FIG. 6B). With this configuration, as head 414 is rotated to change the length of strut 410, code wheel 732 rotates as described above but pulse pattern receiver 734 remains relatively stationary. As such, the rotation of head 414 may be precisely tracked. Preferably, pulse pattern receiver 734 is positioned adjacent code wheel 732 for accurate tracking of the rotation of head 414. As noted above, correction indicator 700 may include a display 720, such as an LCD display, and a battery 725 to power the components of the correction indicator 700.

One correction indicator 700 may be coupled to each strut, either pre-surgery or post-surgery, although mounting post-surgery may be preferable. A user may use a standard driver to rotate the head 414 of each strut 410 according to the correction schedule, with each adjustment tracked and displayed by the correction indicator 700. For example, if the correction schedule indicates that a strut should be rotated three "clicks" per day for ten days, the total number of "clicks" may be displayed on the correction indicator 700 for that strut. After each "click," the correction indicator 700 may display the total number of cumulative "clicks" that the strut 410 has rotated. As such, the patient may reference the correction schedule, for example a paper copy or a computer file, and compare the correction schedule to the information on the display 720 of correction indicator 700 to ensure that the correction is proceeding according to plan. Once a particular strut 410 has been adjusted up to the final adjustment amount, the display 720 may indicate that the correction for the strut 410 is completed to help ensure the user does not over-rotate the strut 410.

Correction indicator 700 may be a lower cost alternative to the motorized tools described above, as well as their non-motorized counterparts, since correction indicator 700 may be used with a fully manual driver to track progress of a correction plan. Correction indicator 700 may include various additional components, such as a transmitter to transmit information relating to progress of adjustment to a computer or other device for viewing by a doctor.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method for tracking progress of a correction plan in an external fixation frame having a plurality of adjustment elements comprising:
   coupling a correction indicator to a first of the plurality of adjustment elements so that a bushing of the correction indicator is rotationally fixed relative to a rotatable head of the first adjustment element and a body of the correction indicator is rotationally fixed relative to a non-rotating portion of the first adjustment element;
   engaging a driver to the rotatable head of the first adjustment element;
   rotating the driver together with the rotatable head and the bushing so that a first tracking element rotationally fixed to the bushing rotates with respect to a second tracking element rotationally fixed to the body; and tracking, via the correction indicator, an amount of rotation of the rotatable head of the first adjustment element.

2. The method of claim 1, further comprising displaying the amount of rotation of the rotatable head of the first adjustment element on a display of the correction indicator.

3. The method of claim 1, wherein the correction indicator includes a battery for powering the correction indicator.

4. The method of claim 1, wherein the driver is a motorized driver.

5. The method of claim 1, wherein the driver is a non-motorized driver.

6. The method of claim 1, wherein the correction indicator is coupled to the first adjustment element prior to coupling the external fixation frame to the patient.

7. The method of claim 1, wherein the correction indicator is coupled to the first adjustment element after coupling the external fixation frame to the patient.

8. The method of claim 1, further comprising coupling additional correction indicators to additional ones of the plurality of adjustment elements so that each adjustment element of the external fixation frame is coupled to one correction indicator.

9. The method of claim 1, wherein the amount of rotation is displayed as a discretized incremental count, each count corresponding to a predetermined value of rotation.

10. The method of claim 9, further comprising displaying the discretized incremental count on the correction indicator.

* * * * *